United States Patent [19]

Little et al.

[11] 4,009,200
[45] Feb. 22, 1977

[54] HEXAHALO-1,4-DIHYDRO-1,4-METHANO-NAPTH-5,8-YLENE ACETATES

[75] Inventors: Julian R. Little, Wayne; Walter Nudenberg, West Caldwell; Yong S. Rim, Paterson, all of N.J.

[73] Assignee: Uniroyal, Inc., New York, N.Y.

[22] Filed: July 8, 1974

[21] Appl. No.: 486,482

Related U.S. Application Data

[62] Division of Ser. No. 329,177, Feb. 2, 1973, Pat. No. 3,875,236, which is a division of Ser. No. 80,747, Oct. 14, 1974, abandoned.

[52] U.S. Cl. ............................................. 260/479 C
[51] Int. Cl.$^2$ ......................................... C07C 53/00
[58] Field of Search ................................ 260/479 R

[56] References Cited

UNITED STATES PATENTS

| | | | |
|---|---|---|---|
| 2,584,139 | 2/1952 | Lidov et al. | 260/586 |
| 2,584,140 | 2/1952 | Segel et al. | 260/625 |
| 3,235,569 | 2/1966 | Dissen | 260/348 |
| 3,277,054 | 10/1966 | Dissen | 260/47 |

*Primary Examiner*—Anton H. Sutto
*Attorney, Agent, or Firm*—Hubbell, Cohen, Stiefel & Gross

[57] ABSTRACT

A fire retardant system comprising a compound having within its structure the 1,2,3,4,9,9-hexahalo-1,4-dihydro-1,4-methanonaphthalene-5,8-dione or 1,2,3,4,9,9-hexahalo-1,4-dihydro-1,4:methanonapthalene-5,8-dioxy nucleus or a compound which is capable of being converted to the 1,2,3,4,9,9-hexahalo-1,4-dihydro-1,4-methanonaphthalene-5,8-dione nucleus and requires no metal oxide addition to exert is function.

6 Claims, No Drawings

HEXAHALO-1,4-DIHYDRO-1,4-METHANO-NAPTH-5,8-YLENE ACETATES

This a division, of application Ser. No. 329,177, filed Feb. 2, 1973, now U.S. Pat. No. 3,875,236, which is in turn a division of application Ser. No. 80,747, filed Oct. 14, 1970, abandoned.

BACKGROUND OF THE INVENTION

1. Field of the Invention

This invention pertains to the field of flame retardants for polymers. More particularly, this invention pertains to improved fire retardant systems for plastics, elastomers, and articles therefrom, e.g., fibers, films, shape articles, and the like.

2. Description of the Prior Art

The increased use of polymeric materials, particularly in the building industry, has resulted in greatly increased interest in the fire retardancy of these materials. However, at the present time most commercially available plastics do not possess satisfactory fire retardancy and this inadequacy represents one of the major obstacles to the opening of new markets and uses for these materials.

Presently, the most widely used fire retardant chemicals are antimony trioxide and organohalogen compounds, the best known being chlorendic anhydride (1,4,5,6,7,7-hexachlorobicyclo-[2.2.1]hept-5-ene-2,3-dicarboxylic anhydride); tetrabromo- or tetrachlorophthalic acid; 1,4'-isopropylidenebis (2,6-dichlorophenol) [tetrachlorobisphenol A] or the corresponding bromine-containing compound; chloran, i.e., 2,3-dicarboxyl-5,8-endomethylene-5,6,7,8,9,9-hexachloro-1,2,3,4,4a,5,8,8a-octahydronaphthalene anhydride; chlorinated paraffins; and dechlorane (dihexachlorocyclopentadiene).

The foregoing halogen compounds have only limited utility in polymer compositions due to a number of disadvantages. For example, when such halogen compounds are incorporated into a polymer, various physical properties of the polymer are modified, e.g., change in melt viscosity which requires higher processing temperatures, decrease in light stability, decrease in thermal stability, increase in density, adverse effects on heat distortion point, etc.

Some of these disadvantages have been overcome by the use of halogen-containing polymers as the flame retardant additive. Typical of such polymers are 2-chlorobutadiene, polyvinylchloride, chlorinated polyethylene and chlorosulfonated polyethylene. There are also, however, serious disadvantages associated with the use of such polymers. Among these are: (1) large amounts of halogen-containing polymers are required in order to obtain satisfactory fire retardancy due to the relatively low halogen content thereof; (2) the halogen-containing polymers have low thermal stabilities; and (3) the blending of the halogen-containing polymer with the polymer to be rendered flame retardant usually requires expensive processing techniques.

SUMMARY OF THE INVENTION

We have discovered a new system of chemical fire retardants for polymeric materials, which system comprises a chemical compound having the 1,2,3,4,9,9-hexahalo-1,4-dihydro-1,4-methanonaphthalene-5,8-dione or 1,2,3,4,9,9-hexahalo-1,4-dihydro-1,4-methanonaphthalene-5,8-dioxy nucleus or a compound which is capable of being converted to the 1,2,3,4,9,9-hexahalo-1,4-dihydro-1,4-methanonaphthalene-5,8-dione nucleus and requires no metal oxide addition to exert its function. Preferably, the compound having the foregoing nucleus or being convertible thereto has a molecular weight not in excess of about 2000.

The polymeric materials are rendered fire retardant by incorporation of the fire retardant system of the present invention into the polymer.

The fire retardant system of the present invention may readily be incorporated into the polymeric material by a variety of methods depending on the nature of the polymeric material. Thus, for example, for those polymers which are adaptable to milling procedures and the like, the fire retardant system may simply be physically blended with the preformed polymer. With other types of polymers which require compounding, e.g., an uncured elastomer, or cannot readily be physically blended with other materials after formation of the polymer, the fire retardant system may be added to the compounding mixture or polymerization mixture.

More particularly, we have found that a polymer may be made effectively flame retardant by blending into the polymer either (1) a fire retardant compound having a nucleus that is of the formula

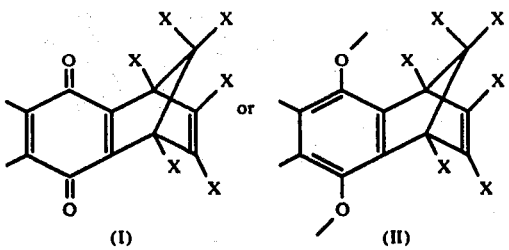

wherein X is halogen, (2) a precursor of said fire retardant compound, which precursor, upon combustion of said blend, converts to a compound containing nucleus I or II, or (3) a fire retardant compound having a nucleus that is of the formula

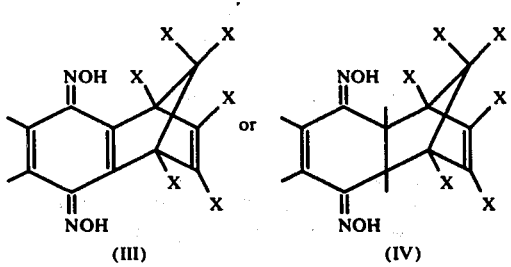

wherein X is halogen.

Preferred precursors contain a nucleus selected from the group consisting of

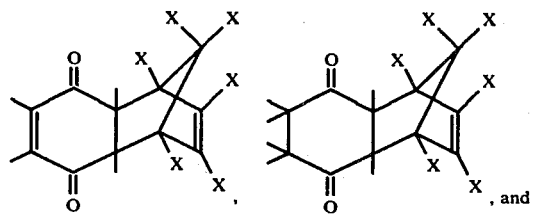

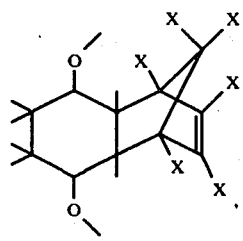

wherein X is halogen.

Most preferred fire retardant compounds are those selected from the group consisting of

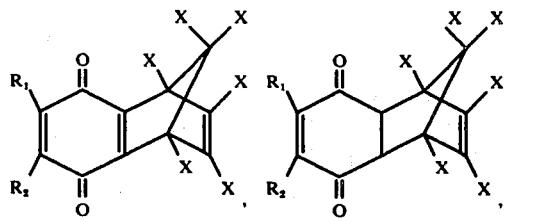

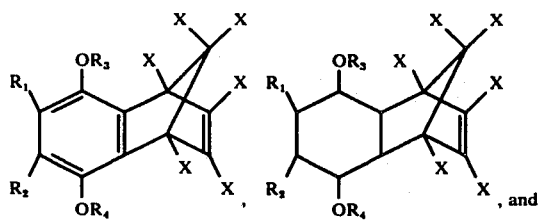

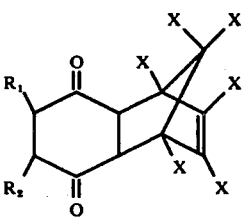

wherein X is halogen, wherein $R_1$ and $R_2$ can be the same or different and each may be
- hydrogen,
- lower alkyl,
- halogen substituted lower alkyl,
- halogen,
- nitrile,
- an aromatic nucleus of the phenyl series,
- $-SO_2R_5$ wherein $R_5$ is lower alkyl, an aromatic nucleus of the phenyl series, or halogen substituted lower alkyl,

wherein $R_6$ is hydrogen, hydroxy, alkoxy, or lower alkyl, or halogen substituted lower alkyl, and wherein $R_1$ and $R_2$ taken together is

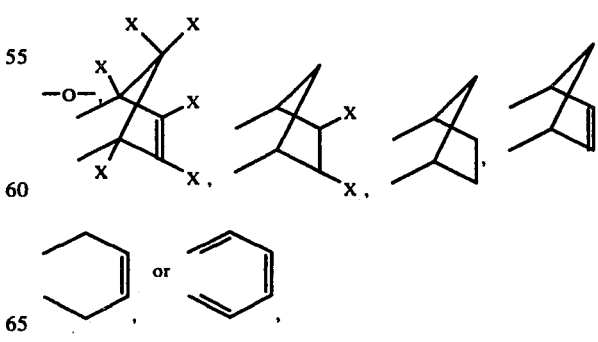

and wherein $R_3$ and $R_4$ are the same or different and each may be hydrogen,
lower alkyl,
halogen substituted lower alkyl,
lower alkanol,
—$(CH_2)_n$ COOH wherein $n$ is an integer from 1 to 5,
—$CH_2CH=CH—R_7$ wherein $R_7$ is hydrogen, lower alkyl, or halogen substituted lower alkyl,
—$SO_2—R_8$ wherein $R_8$ is lower alkyl, an aromatic nucleus of the phenyl series, or halogen substituted lower alkyl,

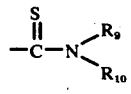

wherein $R_9$ and $R_{10}$ are each lower alkyl, or halogen substituted lower alkyl,

wherein $R_{11}$ and $R_{12}$ are each lower alkoxy,

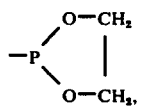

or

wherein $R_{13}$ is lower alkyl, halogen substituted lower alkyl, lower alkoxy, an aromatic nucleus of the phenyl series, or —$NHR_{14}$ wherein $R_{14}$ is lower alkyl.

We have further discovered that when our fire retardant system is incorporated in a polymeric composition containing any of the various previously known fire retardant materials, described hereinabove, the fire retardancy is markedly enhanced to an unexpected degree.

The fire retardant system of the present invention may be used with a wide spectrum of polymeric compositions such as, for example, hydrocarbon chain polymers, natural and synthetic rubbers, resinous or rubbery interpolymers, acrylonitrilebutadiene-styrene polymers, styrene-acrylonitrile resins, foamed and unfoamed polyurethanes, polysulfones, polysulfides, epoxy resins, polyether polyepoxides, thermoplastic and thermosetting polyesters, polycarbonates, cellulose esters, urea-formaldehyde and phenol-formaldehyde resins, polyamides, etc., as well as mixtures of the foregoing with one another.

DESCRIPTION OF THE PREFERRED EMBODIMENTS

The present invention resides in the discovery that polymeric materials may be rendered flame retardant by incorporating therein a fire retardant chemical structural system comprising a compound having within its structure the 1,2,3,4,9,9-hexahalo-1,4-dihydro-1,4-methanonaphthalene-5,8-dione or 1,2,3,4,9,9-hexahalo-1,4-dihydro-1,4-methanonaphthalene-5,8-dioxy nucleus or a compound which is capable of being converted to the 1,2,3,4,9,9-hexahalo-1,4-dihydro-1,4-methanonaphthalene-5,8-dione nucleus and requires no metal oxide addition to exert its function.

Certain of the materials which may be employed as our fire retardant system are novel compounds per se. Such novel compounds include those compounds defined by the following five structural formulas (formulas V-IX respectively). In these formulas "X" always designates halogen:

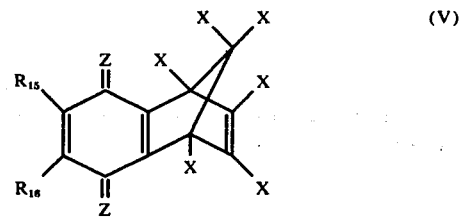

wherein $R_{15}$ and $R_{16}$ are hydrogen or taken together from the group

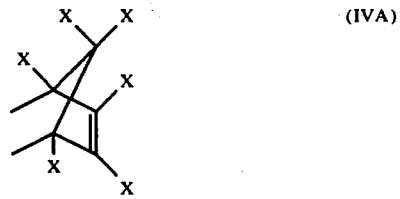

Z is oxygen when $R_{15}$ and $R_{16}$ form the group IVA, and Z is =NOH when $R_{15}$ and $R_{16}$ are hydrogen;

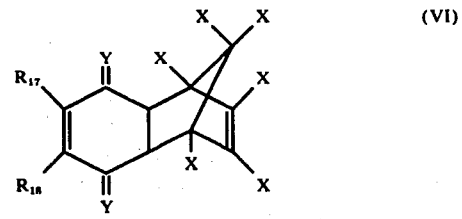

wherein Y is oxygen or =NOH; when Y is oxygen, then $R_{17}$ and $R_{18}$ may be hydrogen, tertiary butyl with at least one of $R_{17}$ and $R_{18}$ being tertiary butyl, or $R_{17}$ and $R_{18}$ taken together form the group IVA; when Y is =NOH, then $R_{17}$ and $R_{18}$ are hydrogen;

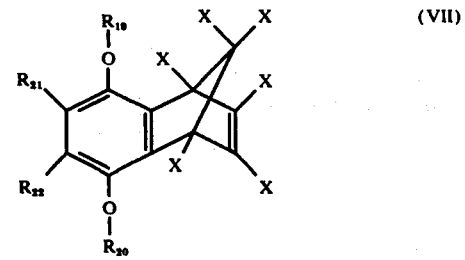

wherein $R_{19}$ and $R_{20}$ are the same or different and each may be
hydrogen,
lower alkyl,
halogen substituted lower alkyl, lower alkanol, —$(CH_2)_n$ COOH wherein $n$ is an integer from 1 to 5, —$CH_2CH=CH-R_{23}$ wherein $R_{23}$ is a hydrogen, halogen substituted lower alkyl, —$SO_2-R_{24}$ wherein $R_{24}$ is lower alkyl, halogen substituted lower alkyl or an aromatic nucleus of the phenyl series,

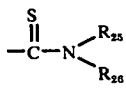

wherein $R_{25}$ and $R_{26}$ are each lower alkyl, or halogen substituted lower alkyl,

wherein $R_{27}$ and $R_{28}$ are each lower alkoxy,

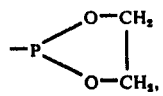

or

wherein $R_{29}$ is lower alkyl, halogen substituted lower alkyl, lower alkoxy, an aromatic nucleus of the phenyl series, or —$NHR_{30}$ wherein $R_{30}$ is lower alkyl, $R_{21}$ and $R_{22}$ can be the same or different and each may be hydrogen, lower alkyl, halogen substituted lower alkyl, —$SO_2-R_{24}$ wherein $R_{24}$ is as defined hereinabove,

wherein $R_{29}$ is as defined hereinabove, with the proviso that when both $R_{19}$ and $R_{20}$ are

then $R_{21}$ and $R_{22}$ may also be halogen, and further provided that when $R_{19}$ and $R_{20}$ are both hydrogen than at least one of $R_{21}$ and $R_{22}$ is a group other than hydrogen or lower alkyl having 1 to 4 carbon atoms, or $R_{21}$ and $R_{22}$ taken together form the group IVA;

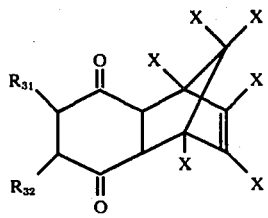

wherein $R_{31}$ and $R_{32}$ may be the same or different and may be hydrogen lower alkyl, halogen substituted lower alkyl, —$SO_2-R_{24}$ wherein $R_{24}$ is as defined hereinabove, —$S-R_{33}$ wherein $R_{33}$ is hydrogen, lower alkyl, or halogen substituted lower alkyl, $R_{31}$ and $R_{32}$ taken together may be —O—,

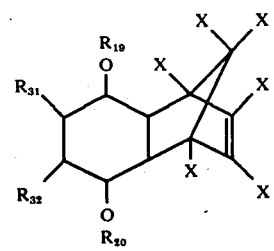

wherein $R_{19}$ $R_{20}$ $R_{31}$ and $R_{32}$ and X are defined hereinabove.

Generally, the compounds of the present invention may be prepared by methods well known in the art for forming [2.2.1] bicyclic ring structures, such as, for example the Diels-Alder reaction. Such synthesis would normally involve the reaction of a hexahalocyclopentadiene with the appropriately substituted benzoquinone compound, to form the structure:

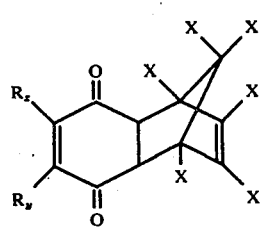

wherein $R_y$ and $R_z$ may be various saturated or unsaturated aliphatic compounds, an aromatic nucleus or functional groups and X is halogen. This compound may then be subjected to various reactions well known in the art for changing the degree of saturation or functional group.

Suitable polymers in which the fire retardant systems of the present invention can be used include:

1. Hydrocarbon chain polymers, such as, for example, polyethylene; cross-linked polyethylene; polypropylene; ethylenepropylene copolymers; polymers of monoethyleneically unsaturated monomers such as styrene, alpha methylstyrene, acrylonitrile, isobutylene, vinyl pyridine, acrylic acid, acrylates, vinyl acetate; vinyl alcohol; vinylethers and copolymers thereof, e.g., ethylenevinylacetate copolymer, etc. Also included are natural and synthetic rubbers, e.g., diene polymers such as polyisoprene (natural or synthetic), or polybutadiene (solution or emulsion prepared); copolymers of dienes with copolymerizable monoethyleneically unsaturated monomers such as styrene, alpha methylstyrene, acrylonitrile, isobutylene, vinyl pyridine, acrylic acid, acrylates, ethylene, propylene, etc. such as butadiene-styrene copolymer, butadiene-acrylonitrile copolymer, and isobutylene-isoprene copolymer. Also suitable are halogen containing hydrocarbon chain polymers with or without plasticizers, such as polyvinylchloride, post chlorinated polyvinylchloride, chlorinated polybutadiene and the like. Suitable hydrocarbon chain polymers are described in U.S. Pat. No. 3,424,821, particularly column 2 thereof, incorporated herein by reference.

2. Also suitable are resinous or rubbery interpolymers having a minor amount of unsaturation, such as rubbery terpolymers of two or more different alpha olefins (usually ethylene and propylene although other pairs of monoolefins may be employed) with a small amount of at least one copolymerizable multiolefin. Usually the multiolefin contains from 5 to 22 carbon atoms and has two double bonds separated by more than two carbon atoms. The multiolefin ordinarily comprises from about 0.5 to not greater than about 20 mole percent of the interpolymer, and the ethylene and propylene units are present in ratios from about 1:4 to about 3:1. Examples of suitable multiolefins are straight or branched chain diolefins, such as those in which both double bonds are terminal as in 1,4-pentadiene, 1,5-hexadiene(biallyl), 2-methyl-1,5-hexadiene, 3,3-dimethyl-1,5-hexadiene, 1,7-octadiene 1,9-decadiene, 1,19-eicosadiene, and the like; diolefins in which only one double bond is terminal such as 1,4-hexadiene, 1,9-octadecadiene, 6-methyl-1,5-heptadiene, 7-methyl-1,6-octadiene, 11-ethyl-1,11-tridecadiene, and similar compounds in which the internal double bond is shielded. Also suitable are the bridged-ring hydrocarbons of similar nature including endocyclic hydrocarbons containing 7 to 10 carbon atoms and two double bonds especially those containing a methylene or an ethylene bridge, for example: (a) unsaturated derivatives of bicyclo[2.2.1] heptane containing at least two double bonds, including bicyclo [2.2.1] hepta-2,5-diene; dicyclopentadiene (also named 3a, 4,7,7a-tetrahydro-4,7-methanoindene), tricyclopentadiene, and tetracyclopentadiene; (b) unsaturated derivatives of bicyclo-[2.2.2] octane containing at least two double bonds, including bicyclo[2.2.2] octa-2,5-diene; (c) unsaturated derivatives of bicyclo [3.2.1] octane containing at least two double bonds; (d) unsaturated derivatives of bicyclo [3.3.1]-nonane containing at least two double bonds; (e) unsaturated derivatives of bicyclo-[3.2.2]-nonane containing at least two double bonds, and the like. Preferred are dicyclopentadiene, 1,4-hexadiene, methylene norbornene and ethylidene norbornene.

Suitable resinous and rubbery interpolymers are described in U.S. Pat. No. 3,361,691, particularly column 1, line 37-column 2, line 3 thereof, and U.S. Pat. Nos. 3,000,866, 3,000,867, 3,063,973, 3,462,399, and 3,489,801, particularly column 1, line 67-column 2, line 35, all of said patents being incorporated by reference herein.

3. Similarly suitable are gum plastics represented by that class of materials combining plastics and rubbers. These materials, also referred to as resin-rubber blends generally comprise a mixture of a hard, relatively brittle polymer (resin) and a minor portion of a relatively soft, rubbery polymer. Particularly well known among this group of polymers are the ABS (acrylonitrile-butadiene-styrene) polymers.

Suitable gum plastics which can be used with the present invention are described in U.S. Pat. No. 3,489,821, particularly column 1, line 52-column 4, line 34 thereof, U.S. Pat. No. 3,489,822, particularly column 1, line 51-column 4, line 45 thereof, said patents being incorporated by reference herein.

The ABS resins which best characterize the gum plastics, are made in a well known manner by interpolymerizing styrene and acrylonitrile monomers in the presence of a rubber which is either polybutadiene or a copolymer of butadiene and styrene, said copolymer containing not more than 10% by weight of combined styrene based on the sum of the weights of butadiene and styrene. Polymerization systems such as emulsion, mass, or solution are also applicable for ABS preparation. The manufacture of such ABS resins is shown in detail in U.S. Pat. Nos. 2,820,773, 2,802,809, 3,238,275, and 3,260,772, particularly column 3, lines 32–50 thereof, each of said patents being incorporated by reference herein. The ABS graft polymer-containing resins used in our invention can be made with varying rubber content, this conveniently being achieved in accordance with known practice (e.g., as shown in U.S. Pat. No. 2,820,773) by admixing additional acrylonitrile-styrene copolymer latex of grafted material, and co-precipitating.

It is further possible to substitute for the acrylonitrile-styrene resinous portion, mixtures of styreneacrylonitrile resin and a vinyl resin such as vinyl chloride polymer (particularly polyvinyl chloride).

In place of using acrylonitrile itself for the preparation of the polymer, one may substitute for some or all of the acrylonitrile, equivalent similar monomers such as homologs or substitution products of acrylonitrile, e.g., methacrylonitrile, ethacrylonitrile, methyl acrylate, and the like.

Similarly, in place of using styrene itself in the preparation of the polymers used in the invention, one may substitute for some or all of the styrene, equivalent monomers including substitution products of styrene, such as alkyl-substituted styrenes, including alpha-alkyl styrenes and nuclear alkyl-substituted styrenes such as alpha-methyl-styrene, other nuclear methyl-substituted styrenes, nuclear monoethyl-substituted styrenes, the mono- and di-chloro styrenes, etc.

4. Further suitable are foamed and unfoamed rigid polyurethanes, i.e., organic diisocyanate-modified polyesters, polyethers, polyester-polyethers and polyester-polyamides, both saturated and olefinically unsaturated. Such polymers are generally obtained from the reaction of a polyisocyanate, usually a diisocyanate, with a polyfunctional compound containing active-hydrogen groups, such as hydroxy-terminated polyesters, castor oil, polyester amides and polyalkylene ether glycols as well as mixtures of two or more of these classes of polyfunctional compounds. The material used for reaction with the polyisocyanate to make the polyurethane is frequently a polyether or polyester glycol having a molecular weight of from 400 to 6000, preferably in the 1000–2000 range. Mention may be made of chain extended polyesters made from a glycol (e.g. ethylene and/or propylene glycol) and a saturated dicarboxylic acid (e.g. adipic acid). Usually the starting glycol contains from 2 to 20 carbon atoms and the acid contains from 4 to 12 carbon atoms. Polyethylene adipate, polyethylene adipate-phthalate, polyneopentyl sebacate, etc. may be mentioned. Small amounts of tri-alcohols such as trimethylolpropane or trimethylolethane may be included. There may also be mentioned the polyethers, such as polypropylene glycol, polypropylene-ethylene glycol and polytetramethylene glycol. Among the suitable polyisocyanates may be mentioned m- and p-phenylene diisocyanates; toluene diisocyanate; p,p'-diphenylmethane diisocyanate; 3,3'-dimethyl (or dimethoxy)-4,4'-biphenyl diisocyanate; 1,5-naphthylene diisocyanate; p,p',p''-triphenylmethane triisocyanate; p-phenylene diisothiocyanate, etc. The isocyanate is, of course, used in an amount at least equivalent to the hydroxyl groups in the starting polymer; larger quantities of diisocyanate favor formation of liquid prepolymer. Generally the molar ratio of diisocyanate to glycol is in the 1.2:1 to 3:1 range. For additional examples of (e.g., adipic starting materials for making polyurethanes, reference may be had to the following: Otto Bayer in "Angewandte Chemie," A/59 (1947), No. 9, p. 264; and U.S. Pat. No. 3,105,062 incorporated herein by reference. Suitable polyurethanes are described in U.S. Pat. No. 3,412,071, particularly column 5, line 44-column 4, line 6 thereof, U.S. Pat. Nos. 2,734,045 and 3,457,326, each of said patents being incorporated by reference herein.

5. Also suitable are polysulfones. Such polysulfones have a basic structure of recurring units having the formula

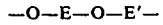

wherein E is the residuum of a dihydric phenol and E' is the residuum of the benzenoid compound having an inert electron withdrawing group in at least one of the positions ortho and para to the valence bonds, where both of said residua are valently bonded to the ether oxygens through aromatic carbon atoms and wherein at least one of E or E' is dinuclear and at least one of the pair of nuclei are joined by a sulfone (—$SO_2$—) group.

The residuum E of the dihydric phenol can be, for instance, a mononuclear phenylene group as results from hydro-quinone and resorcinol, or it may be a di- or polynuclear residuum. The residuum E can also be substituted with other inert nuclear substituents such as halogen, alkyl, alkoxy and like inert substituents.

It is preferred that the dihydric phenol be a weakly acidic dinuclear phenol such as, for example, the dihydroxy diphenyl alkanes or the nuclear halogenated derivatives thereof, which are commonly known as "bisphenols," such as, for example, the 2,2-bis-(4-hydroxyphenyl)propane, 1,1-bis-(4-hydroxyphenyl)-2-phenylethane, bis-(4-hydroxyphenyl)methane, or the chlorinated derivatives containing one or two chlorines on each aromatic ring. Other suitable dinuclear dihydric phenols are the bisphenols of a symmetrical or unsymmetrical joining group as, for example, ether oxygen (—O—), carbonyl (—CO—), sulfide (—S—), sulfone (—$SO_2$—) or hydrocarbon residue in which the two phenolic nuclei are joined to the same or different carbon atoms of the residue such as, for example, the bisphenol of acetophenone, the bisphenol of benzophenone, the bisphenol of vinyl cyclohexane, the bisphenol of α-pinene, and the like bisphenols where the hydroxyphenyl groups are bound to the same or different carbon atoms of an organic linking group.

Such dinuclear phenols can be characterized as having the structure:

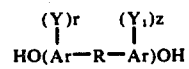

wherein Ar is an aromatic group and preferably is a phenylene group, Y and $Y_1$ can be the same or different inert substituent groups as alkyl groups having from 1 to 4 carbon atoms, halogen atoms, i.e., fluorine, chlorine, bromine, or iodine, or alkoxy radicals having from 1 to 4 carbon atoms, r and z are integers having a value of from 0 to 4, inclusive, and R is representative of a bond between aromatic carbon atoms as in dihydroxydiphenyl, or is a divalent radical, including for example, inorganic radicals as —CO—, —O—, —S—, —S—S—, —$SO_2$—, and divalent organic hydrocarbon radicals such as alkylene, alkylidene, cycloaliphatic, or the halogen, alkyl, aryl or like substituted alkylene, alkylidene and cycloaliphatic radicals as well as alkalicyclic, alkarylene and aromatic radicals and a ring fused to both Ar group.

Examples of specific dihydric polynuclear phenols include among others: the bis-(hydroxyphenyl)alkanes such as
2,2bis(4-hydroxyphenyl)propane,
2,4'-dihydroxydiphenyl-methane,
bis-(2-hydroxyphenyl)methane,
bis-(4-hydroxyphenyl)methane,
bis-(4-hydroxy-2,6-dimethyl-3-methoxyphenyl)methane,
1,1-bis-(4-hydroxyphenyl)ethane,
1,2-bis-(4-hydroxyphenyl)ethane,
1,1-bis-(4-hydroxy-2-chlorophenyl)ethane,
1,1-bis-(3-methyl-4-hydroxyphenyl)propane,
1,3-bis-(3-methyl-4-hydroxyphenyl)propane,
2,2-bis-(3-phenyl-4-hydroxyphenyl)propane,
2,2-bis-(3-isopropyl-4-hydroxyphenyl)propane,
2,2-bis-(2-isopropyl-4-hydroxyphenyl)propane,
2,2-bis-(4-hydroxynaphthyl)propane,
2,2-bis-(4-hydroxyphenyl)pentane,
3,3-bis-(4-hydroxyphenyl)pentane,
2,2-bis-(4-hydroxyphenyl)heptane,
bis-(4-hydroxyphenyl)phenylmethane,
2,2-bis-(4-hydroxyphenyl)-1-phenylpropane,
2,2-bis-(4-hydroxyphenyl)-1,1,1,3,3,3-hexafluoropropane and the like;
Di(hydroxyphenyl)sulfones such as bis-(4-hydroxyphenyl)-sulfone, 2,4'-dihydroxydiphenyl sulfone, 5'-chloro-2,4'-dihydroxydiphenyl sulfone, 5'-chloro-4,4'-dihydroxydiphenyl sulfone, and the like;
Di(hydroxyphenyl)ethers such as bis-(4-hydroxyphenyl)-ether, the 4,3'-, 4,2'-, 2,2'-, 2,3'-dihydroxydiphenyl ethers, 4,4'-dihydroxy-2,6-dimethyldiphenyl ether, bis-(4-hydroxy-3-isobutylphenyl)ether, bis-(4-hydroxy-3-isopropylphenyl)ether, bis-(4-hydroxy-3-chlorophenyl)-ether, bis-(4-hydroxy-3-fluorophenyl)ether, bis-(4-hydroxy-3-bromophenyl)ether, bis-(4-hydroxynaphthyl)-ether, bis-(4-hydroxy-3-chloronaphthyl)ether, 4,4'-dihydroxy-3,6-dimethoxydiphenyl ether, 4,4'-dihydroxy-2,5-diethoxydiphenyl ether, and like materials.

It is also contemplated to use a mixture of two or more different dihydric phenols to accomplish the same ends as above. Thus, when referred to above, the E residuum in the polymer structure can actually be the same or different aromatic residua.

As used herein, the E term defined as being the "residuum of the dihydric phenol" refers to the residue of the dihydric phenol after the removal of the two aromatic hydroxy groups. Thus, it is readily seen that polyarylene polyethers contain recurring groups of the residuum of the dihydric phenol and the residuum of the benzenoid compound bonded through aromatic ether oxygen atoms.

The residuum E' of the benzenoid compound can be from any dihalobenzenoid compound or mixture of di-halobenzenoid compounds which compound or compounds have the two halogens bonded to benzene rings having an electron withdrawing group in at least one of the positions ortho and para to the halogen group. The dihalobenzenoid compound can be either mononuclear where the halogens are attached to the same benzenoid ring or polynuclear where they are attached to different benzenoid rings, as long as there is the activating electron withdrawing group in the ortho or para position of that benzenoid nucleus.

Any of the halogens may be the reactive halogen substituents on the benzenoid compounds, fluorine and chlorine substituted benzenoid reactants being preferred.

Any electron withdrawing group can be employed as the activator group in the dihalobenzenoid compounds. Preferred are the strong activating groups such as the sulfone group (—SO$_2$—) bonding two halogen substituted benzenoid nuclei as in the 4,4'-dichlorodiphenyl sulfone and 4,4'-difluorodiphenyl sulfone, although such other strong withdrawing groups hereinafter mentioned can also be used with ease. It is further preferred that the ring contain no electron supply groups on the same benzenoid nucleus as the halogen; however, the presence of other groups on the nucleus or in the residuum of the compound can be tolerated. Preferably, all of the substituents on the benzenoid nucleus are either hydrogen (zero electron withdrawing), or other groups having a positive sigma value, as set forth in J. F. Bunnett in Chem. Rev., 49,273 (1951) and Quart. Rev., 12,1 (1958).

The electron withdrawing group of the dihalobenzenoid compound can function either through the resonance of the aromatic ring, as indicated by those groups having a high sigma value, i.e. above about +0.7 or by induction as in perfluro compounds and like electron sinks.

Preferably the activating groups should have a high sigma value, preferably above 1.0, although sufficient activity is evidenced in those groups having a sigma value above 0.7.

The activating group can be basically either of two types:

a. monovalent groups that activate one or more halogens on the same ring as a nitro group, phenylsulfone, or alkylsulfone, cyano, trifluoromethyl, nitroso, and hetero nitrogen as in pyridine.

b. divalent groups which can activate displacement of halogens on two different rings, such as the sulfone group —SO$_2$—; the carbonyl group —CO—; the vinyl group —CH=CH—; the sulfoxide group —SO—; the azo group —N=N—; the saturated fluorocarbon group

—CF$_2$CF$_2$—;

organic phosphine oxides

where R is a hydrocarbon group; and the ethylidene group

where X can be hydrogen or halogen or divalent groups which can activate halogens on the same ring such as with diflurobenzoquinone, 1,4- or 1,5- or 1,8-difluoroanthraquinone.

If desired, the polymers may be made with mixtures of two or more dihalobenzenoid compounds each of which has this structure, and which may have different electron withdrawing groups. Thus, the E' residuum of the benzenoid compounds in the polymer structure may be the same or different.

It is seen also that as used herein, the E' term defined as being the "residuum of the benzenoid compound" refers to the aromatic or benzenoid residue of the compound after the removal of the halogen atoms on the benzenoid nucleus. Suitable polysulfones are described in U.S. Pat. No. 3,365,517, particularly columns 2–6 thereof, incorporated by reference herein.

6. Also suitable are epoxy resins formed from polyepoxides and an epoxy curing agent. The polyepoxide may be any material having more than one epoxy group, i.e., more than one

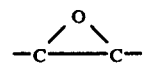

group, an epoxy equivalency per 100 grams greater than 0.20 as determined by standard analysis, and preferably a molecular weight below 900. These polyepoxides may be saturated or unsaturated and aliphatic, cycloaliphatic and aromatic and may be substituted with substituents, such as chlorine atoms, hydroxyl groups, alkoxy radicals and the like.

Examples of these polyepoxides include, among others, vinyl cyclohexene dioxide, 2,3,5,6-diepoxyoctane, 2,3,6,7-diepoxydodecane, 1,2-epoxy-3-(2,3-epoxypropyl)cyclohexane, 1,2-epoxy-4-epoxybutyl)cyclohexane, epoxidized triglycerides such as epoxidized glycerol trioleate and epoxidized glycerol trilinoleate, the monoacetate of epoxidized glycerol dioleate bis(2,3-epoxycyclopentyl)ether, and the like.

Other polyepoxides comprise the polyepoxy polyethers obtained by reacting, preferably in the presence of an acid-acting compound, such as hydrofluoric acid, one of the aforedescribed halogen-containing epoxides with a polyhydric alcohol, and subsequently treating the resulting product with an alkaline component. As used herein and in the claims, the expression "polyhydric alcohol" is meant to include those compounds having at least two free alcoholic OH groups and includes the polyhydric alcohols and their ethers and esters, hydroxy-aldehydes, hydroxy-ketones, halogenated polyhydric alcohols and the like.

Polyhydric alcohols that may be used for this purpose may be exemplified by glycerol, propylene glycol, ethylene glycol, diethylene glycol, butylene glycol, hexanetriol, sorbitol, mannitol, pentaerythritol, polyallyl alcohol, polyvinyl alcohol, inositol, trimethylolpropane, bis(4-hydroxycyclohexyl)dimethylmethane, 1,4-dimethylolbenzene, 4,4′-dimethyloldiphenyl, dimethyloltoluenes, and the like. The polyhydric ether alcohols include, among others, diglycerol, triglycerol, dipentaerythritol, tripentaerythritol, dimethylolanisoles, beta-hydroxyethyl ethers of polyhydric alcohols, such as diethylene glycol, polyethylene glycols, bis(beta-hydroxyethyl ether) of bis-phenol, betahydroxyethyl ethers of glycerol, pentaerythritol, sorbitol, mannitol, etc., condensates of alkylene oxides, such as ethylene oxide, propylene oxide, butylene oxide, isobutylene oxide, glycidyl, epichlorohydrin, glycidyl ethers, etc., with polyhydric alcohols, such as the foregoing and with polyhydric thioesters, such as 2,2′-dihydroxy diethyl sulfide, 2,2′-3,3′-tetrahydroxy dipropyl sulfide, etc. The hydroxy-aldehydes and ketones may be exemplified by dextrose, fructose, maltose, glyceraldehyde. The mercapto (thio) alcohols may be exemplified by alpha-monothioglycerol, alpha, alpha-dithioglycerol, etc. The polyhydric alcohol esters may be exemplified by monoglycerides, such as monostearin, monoesters of pentaerythritol and acetic acid, butyric acid, pentanoic acid, and the like. The halogenated polyhydric alcohols may be exemplified by the monochloride of pentaerythritol, monochloride of sorbitol, monochloride of mannitol, monochloride of glycerol, and the like.

Coming under special consideration are the polyglycidyl polyethers of polyhydric alcohols obtained by reacting the polyhydric alcohol with epichlorohydrin, preferably in the presence of 0.1% to 5% by weight of an acid-acting compound, such as boron trifluoride, hydrofluoric acid, stannic chloride or stannic acid. This reaction is effected at about 50° to 125° C with the proportions of reactants being such that there is about one mole of epichlorohydrin for every equivalent of hydroxyl group in the polyhydric alcohol. The resulting chlorohydrin ether is then dehydrochlorinated by heating at about 50° to 125° C with a small, e.g., 10% stoichiometrical excess of a base, such as sodium aluminate.

The products obtained by the method shown in the preceding paragraph may be described as polyether polyepoxide reaction products which in general contain at least three non-cyclic ether (—O—) linkages, terminal epoxide-containing ether

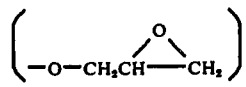

groups and halogen attached to a carbon of an intermediate

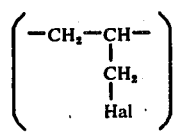

group.

These halogen-containing polyether polyepoxide reaction products obtainable by partial dehydrohalogenation of polyhalohydrin alcohols may be considered to have the following general formula

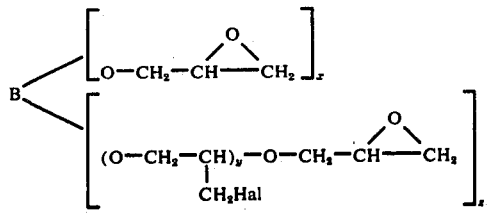

in which R is the residue of the polyhydric alcohol which may contain unreacted hydroxyl group, Y indicates one or more of the epoxy ether groups attached to the alcohol residue, y may be one or may vary in different reaction products of the reaction mixture from zero to more than one, and Z is one or more, and X+Z, in the case of products derived from polyhydric alcohols containing three or more hydroxyl groups, averages around two or more so that the reaction product contains on the average two or more than two terminal epoxide groups per molecule.

The epoxy curing agent employed in the impregnating solution may be any alkaline, neutral or acidic compound which acts to effect cure of the polyepoxide to form an insoluble product. The epoxy curing agent is preferably neutral or alkaline. Examples of curing agents include, among others, alkalies like sodium or potassium hydroxides; alkali phenoxides like sodium phenoxide; carboxylic acids or anhydrides, such as formic acid, oxalic acid or phthalic anhydride; Friedel-Crafts metal halides like aluminum chloride, zinc chloride, ferric chloride or boron trifluoride as well as complexes thereof with ethers, acid anhydrides, ketones, diazonium salts, etc.; salts, such as zinc fluoborate, magnesium perchlorate and zinc fluosilicate; phosphoric acid and partial esters thereof including n-butyl ortho-phosphate, diethyl ortho-phosphate and hexethyl tetraphosphate, amino compounds, such as, for example, diethylene triamine, triethylene tetraamine, dicyandiamide, melamine, pyridine, cyclohexylamine, benzyldimethylamine, benzylamine, diethylaniline, triethanolamine, piperidine, tetramethyl piperazine, N,N-dibutyl-1,3-propane diamine, N,N-diethyl-1,3-propane diamine, 1,2-diamino-2-methylpropane, 2,3diamino-2-methylbutane, 2,4-diamino-2-methylpentane, 2-diamino-2,6-dimethyloctane, dibutylamine, dioctylamine, dinonylamine, distearylamine, diallylamine, dioleylamine, dicyclohexylamine, methylethylamine, ethylcyclohexylamine, o-tolylnaphthylamine, pyrrolidine, 2-methylpyrrolidine, tetrahydropyridine, 2-methylpiperidine, 2,6-dimethylpiperidine, diaminopyridine, tetraethylene pentamine, metaphenylene diamine, and the like; and soluble adducts of amines and polyepoxides and their salts, such as described in U.S. Pat. No. 2,651,589 and U.S. Pat. No. 2,640,037 incorporated herein by reference.

Preferred curing agents include the alkaline or neutral materials and more preferably the amine, polyepoxide amine adducts or their neutral salts. Coming under special consideration are the mono- and polyamines, such as those of the formulae

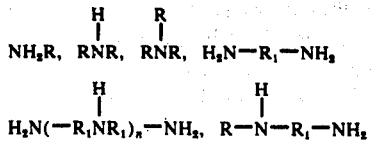

wherein R is a monovalent hydrocarbon radical and $R_1$ is a bivalent hydrocarbon radical containing no more than 18 carbon atoms and $n$ is an integer, preferably from 1 to 8. Particularly preferred are the aliphatic polyamines having a molecular weight below 250.

Suitable polyepoxides are described in U.S. Pat. No. 2,902,398, incorporated herein by reference.

7. Also suitable are both thermoplastic and thermosetting polyesters. Suitable thermoplastic polyesters are condensation polymers of dihydric alcohols with organo-dibasic acids, particularly dicarboxylic acids, and self-condensation polymers of omega-hydroxy carboxylic acids, the preferred materials being poly(ethylene terephthalate), poly(ethylene terephthalate-isophthalate), and poly(1,4-cyclohexylenedimethylene terephthalate). Applicable are all film- and fiber-forming polyesters, in which the ester linkages are intralinear, including poly(alkylene alkanedioates), poly(cycloalkylenedimethylene alkanedioates), poly(alkylene arenedioates), poly(cycloalkylenedimethylene arenedioates), and analogous materials. Examples of the above-named polyesters are respectively, poly(ethylene adipate), poly(1,4-cyclohexylenedimethylene adipate), poly(ethylene terephthalate), and poly(1,4-cyclohexylenedimethylene terephthalate). Suitable thermoplastic polyesters are described in U.S. Pat. No. 3,410,749, incorporated herein by reference.

7a. The thermosetting polyesters are mixtures of unsaturated polyester resins with copolymerizable ethylenically unsaturated monomers. Under the influence of various catalytic or promoting substances, these resinous compositions, which are intially liquid, or dough-like materials can be converted into solid, insoluble and infusible shapes. This transformation is essentially a copolymerization of the unsaturated polyester with the added monomer, leading to a cross-linked polymer of exceedingly high molecular weight.

The unsaturated polyester resin may be defined as a self-condensation product of an ester of a polyhydric alcohol with a polycarboxylic acid, at least one of which is unsaturated. Frequently the unsaturated polyester is made from one or more glycols and one or more alpha, beta-ethylenically unsaturated polycarboxylic acids. By way of non-limiting example, it may be mentioned that polyesters can be prepared from such acids as maleic, fumaric, aconitic, mesaconic, citraconic, ethylmaleic, pyrocinchoninic, veronic, or itaconic acid (with or without such acids as adipic, succinic, sebacic, phthalic, etc., or such acids as linolenic, linoleic, elaeosteric, etc.) with such glycols as ethylene, diethylene, triethylene, polyethylene, 1,3-propylene, 1,2-propylene, dipropylene (1,3 or 1,2), butylene or styrene glycol.

The copolymerizable ethylenically unsaturated monomers suitable for mixing with the foregoing unsaturated polyesters to produce the desired thermosetting composition are also well-known. Among the more important of such monomers may be mentioned styrene, vinyl toluene, methyl methacrylate, vinyl acetate, diallyl phthalate and triallyl cyanurate. Suitable thermosetting polyesters are described in U.S. Pat. No. 3,267,055, incorporated herein by reference.

8. Further suitable polymers are polycarbonates which may be prepared by reacting a dihydric phenol with a carbonate precursor such as phosqene, a haloformate, or a carbonate ester. Generally speaking, such carbonate polymers can be typified recurring structural units of the formula

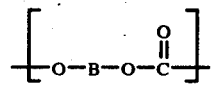

where B is a divalent aromatic radical of the dihydric phenol employed in the polymer producing reaction. The dihydric phenols which may be employed to provide such aromatic carbonate polymers are mononuclear or polynuclear aromatic compounds, containing as functional groups, 2 hydroxy radicals, each of which is attached directly to a carbon atom of an aromatic nucleus.

Typical dihydric phenols are
2,2-bis-(4-hydroxyphenyl)propane,
hydroquinone,
resorcinol,
2,2-bis-(4-hydroxyphenyl) pentane,
2,4-dihydroxy diphenyl methane,
bis-(2-hydroxyphenyl)methane,
bis-(4-hydroxyphenyl)methane,
bis-(4-hydroxy-5-nitrophenyl)methane,
1,1-bis-(4-hydroxyphenyl)ethane,
3,3-bis-(4-hydroxyphenyl)pentane,
2,2'-dihydroxydiphenyl,
2,6-dihydroxy naphthalene,
bis-(4-hydroxyphenyl)sulfone,
2,4'-dihydroxydiphenyl sulfone,
5'-chloro-2,4'-dihydroxydiphenyl sulfone,
bis-(4-hydroxyphenyl)diphenyl disulfone,
4,4'-dihydroxyphenyl ether,
4,4'-dihydroxy-3,3'-dichlorodiphenyl ether, and
4,4'-dihydroxy-2,5-diethoxydiphenyl ether.

A variety of additional dihydrophenols which may be employed to provide such carbonate polymers are disclosed in U.S. Pat. No. 2,999,835. It is, of course, possible to employ two or more different dihydric phenols, or a dihydric phenol in combination with a glycol, a hydroxy terminated polyester, or a dibasic acid in the event a carbonate copolymer rather than a homopolymer is desired for use in the preparation of the mixtures of the invention.

When a carbonate ester is used as the carbonate precursor in the polymer forming reaction, the materials are reacted at temperatures of from 100° C. or higher for times varying from 1 to 15 hours. Under such conditions ester interchange occurs between the carbonate ester and the dihydric phenol used. The ester interchange is advantageously consummated at reduced pressures of the order of from about 10 to about 100 mm. of mercury, preferably in an inert atmosphere, such as nitrogen or argon, for example.

Although the polymer forming reaction may be conducted in the absence of a catalyst, one may, if desired, employ the usual ester exchange catalysts, such as, for example, metallic lithium, potassium, calcium and magnesium. Additional catalysts and variations in the exchange methods are discussed in Groggins, Unit Processes in Organic Synthesis (4th edition, McGraw-Hill Book Company, 1952), pages 616 to 620. The amount of such catalyst, if used, is usually small, ranging from about 0.001 to about 0.1%, based on the moles of the dihydric phenol employed.

The carbonate ester useful in this connection may be aliphatic or aromatic in nature, although aromatic esters, such as diphenyl carbonate, are preferred. Additional examples of carbonate esters which may be used are dimethyl carbonate, diethyl carbonate, phenyl methyl carbonate, phenyltolyl carbonate and di(tolyl) carbonate. Suitable polycarbonates are described in U.S. Pat. No. 3,365,517, particularly columns 6 and 7.

9. Additionally suitable are cellulose esters and nitrocellulose based coatings including cellulose acetate, cellulose acetate propionate, cellulose acetate butyrate, ethyl cellulose, cellulose nitrate, etc. Cellulose acetate esters are prepared by the reaction of chemical cellulose with acetic acid and acetic anhydride, sulfuric acid generally being used as a catalyst. Ethyl cellulose is an ether and manufactured by the reaction of chemical cellulose with caustic to form alkali cellulose, which then reacts with ethyl chloride to form ethyl cellulose. Cellulose nitrate is also referred to as nitrocellulose and is prepared by the nitration of chemical cellulose, using sulfuric acid as catalyst and dehydrating agent, 10. Formaldehyde resins, for example, phenol formaldehyde resins and urea-formaldehyde resins as described in *The Encyclopedia of Polymer Science and Technology*, Interscience, 1969 Edition, Volume 10, pages 1–73 and Volume 2, pages 25–42, respectively.

11. Polyamides — including polyaminated derivatives of carboxylic acids, the structural units being connected by amide or thioamide groupings having the general formula:

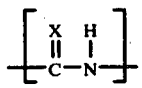

wherein X is O or S.

Such polyamides are generally formed by the reaction of dicarboxylic acids with diamines, such as, adipic acid and hexamethylene diamine, from omega-amino acids, or by a ring opening reaction of lactams such as epsilon-caprolactam. Other suitable fiber forming polyamides are described in U.S. Pat. Nos. 2,071,250, 2,071,253, 1,130,523 and 2,130,948, incorporated herein by reference.

Normally, the amount of fire retardant used depends on the nature of the polymer and the proposed end use. It is thus well within the knowledge of the skilled art worker to select the optimum content of the fire retardant system of the present invention for any given polymer. Generally, however, the amount of fire retardant is sufficient to produce a halogen content in the polymer of preferably from about 1 to 20 percent by weight of the composition and most preferably from about 2 to 13 percent by weight of the composition.

EXAMPLE 1

Preparation of 1,2,3,4,9,9-hexachloro-1,4,4a,8a-tetrahydro-1,4-methanonaphthalene-5,8-dione A mixture of 54.6 g. (0.2 mole) of hexachlorocyclopentadiene, 21.6 g. (0.2 mole) of p-benzoquinone, and 10 ml. of toluene were placed in a 125 ml. round bottom flask and heated for three hours so that the toluene refluxed gently. At the end of this period the reaction mixture suddenly solidified completely, indicating completion of the reaction. The crude product was bright yellow. The damp material was transferred to a Buchner funnel, rinsed with absolute ethanol, dried on the funnel, and crystallized from ethanol. 49 g. of bright yellow dense crystals were obtained, m.p. 189°–193° C (reported 188° C). The yield was 64%.

The product has the following structure:

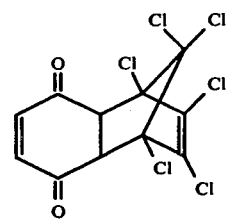

EXAMPLE 2

Preparation of 1,2,3,4,9,9-hexachloro-1,4-dihydro-1,4-methano naphthalene-5,8-diol 50 g. of the dione prepared according to Example 1 were dissolved in 300 ml. of methanol and 3 g. of pyridine were added. The mixture was refluxed until the yellow color disappeared (about 5 hours). Upon cooling to 5°–7° C, white crystals separated. One recrystallization from methanol gave white crystals, m.p. 186° C. The yield was almost quantitative.

The product has the following structure:

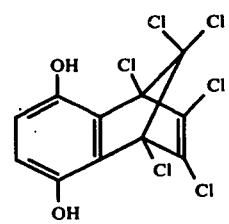

EXAMPLE 3

Preparation of 1,2,3,4,9,9-hexachloro-1,4-dihydro-1,4-methanonaphthalene-1,8-dione.

38 g. of the diol prepared according to Example 2 were dissolved in 300 ml. anhydrous ether and 30 g. of anhydrous Na$_2$SO$_4$ and 29 g. of Ag$_2$O were added to this solution. The reaction mixture was shaken on a Parr Shaker until the color turned to deep orange (about 20 minutes). Filtration and evaporation of the ether produced an orange colored solid. One recrystallization from hexane-benzene mixture gave orange crystals, m.p. 118°–119° C. The yield was about 70 percent.

The product has the following structure:

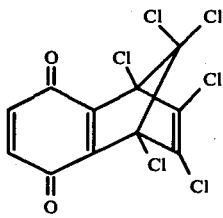

EXAMPLE 4

Reaction product of 1,2,3,4,9,9-hexachloro-1,4-dihydro-1,4-methanonaphthalene-5,8,-dione and hydroxylamine.

19 g. of 1,2,3,4,9,9-hexachloro-1,4-dihydro-1,4-methanonaphthalene-5,8-dione prepared in accordance with Example 3, were dissolved in 150 ml. of 95% ethanol and 8 g. of hydroxylamine hydrochloride were added. Then 11g. of potassium bicarbonate were added in small increments. A slight exotherm occurred during the potassium bicarbonate addition. After 24 hours of stirring, the mixture was poured into cold water, and a light brown solid was obtained. Infrared spectrum showed no carbonyl and medium intensity absorption at 1590 cm$^{-1}$.

The product has the following structure:

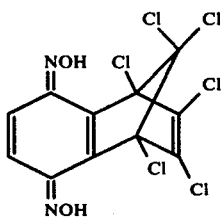

EXAMPLE 5

Preparation of 1,2,3,4,5,6,7,8,11,11,12,12-dodecachloro-1,4,4a, 5, 8, 9a-hexahydro-1,4:5,8-dimethanoanthracene-9,10-dione.

38 g. of 1,2,3,4,9,9,-hexachloro-1,4-dihydro-1,4-methanonaphthalene-5,8-dione prepared in accordance with Example 3 were mixed with 30 g. of hexachlorocyclopentadiene and 30 ml. of toluene, and refluxed for 6 hours. By cooling to room temperature, yellow crystals were formed and were washed with cold Skelly B solvent. One recrystallization from benzene-hexane 50/50 mixed solvent gave yellow crystals, m.p. 234°–235° C.

| | Calculated | Observed | |
|---|---|---|---|
| | | Test 1 | Test 2 |
| C | 29.4% | 28.94 | 28.96 |
| H | 0.3 % | 0.52 | 0.37 |
| Cl | 65.3 | 64.07 | 64.25 |

The product has the following structure:

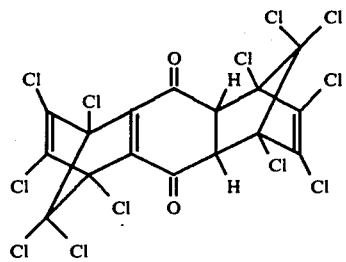

EXAMPLE 6

Preparation of 1,2,3,4,5,6,7,8,11,11,12,12-dodecachloro-1,4,5,8-tetrahydro-1,4:5,8-dimethanoanthracene-9,10-diol.

49 g. of 1,2,3,4,5,6,7,8,11,11,12,12-dodecachloro-1,4,4a,5,8,-9a-hexahydro--dimethanoanthracene-9,10-dione prepared in accordance with Example 5, were dissolved in methanol and a few drops of pyridine were added. When warmed to about 45° C, the yellow solution became colorless and the isomerization was complete. After cooling to 5°-7° C. and filtration, white crystals were obtained. One recrystallization from methanol gave white crystals, m.p. 329° C.

| | Calculated | Observed | |
|---|---|---|---|
| | | Test 1 | Test 2 |
| C | 29.4% | 29.6 | 29.7 |
| H | 0.3 % | 0.33 | 0.49 |
| Cl | 65.3 % | 64.97 | 64.04 |

The product had the following structure:

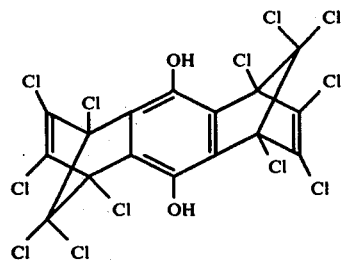

EXAMPLE 7

Preparation of 1,2,3,4,5,6,7,8,11,11,12,12-dodecachloro-1,4,5,8, tetrahydro-1,4:5,8-dimethanoanthracene-9,10-dione.

23 g. of 1,2,3,4,5,6,7,8,11,11,12,12-dodecachloro-1,4,5,8-tetrahydro-1,4:5,8-dimethanoanthracene-9,10-diol, prepared in accordance with Example 6, were dissolved in 150 ml. of anhydrous ether. Anhydrous sodium sulfate, 10 g., and 12 g. of silver oxide were added and the mixture was shaken for two hours (Parr shaker). After filtration, the deep red ether solution was evaporated and crude red crystals were obtained. One recrystallization from 50/50 benzene-Skelly B solution gave red crystals, m.p. 282°–283° C.

| Calculated | Observed | |
|---|---|---|
| | Test 1 | Test 2 |
| Cl 65.5% | 64.58 | 64.50 |

The product has the following structure:

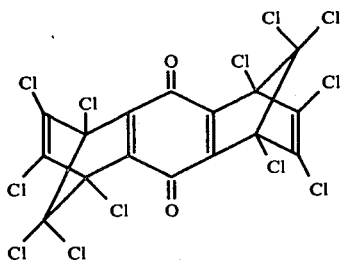

EXAMPLE 8 preparation of 6-tert-butyl-1,2,3,4,9,9-hexachloro-1,4,4a,8a-tetrahydro-1,4-methanonaphthalene-5,8-dione.

30 g. of tert-butylhydroquinone (Eastman-Kodak) were dissolved in 200 ml. of anhydrous ether and 30 g. of anhydrous sodium sulfate were added. To this mixture was added 60 g. of silver oxide in small increments. An exothermic reaction ensued. After shaking for 20 minutes, the reaction mixture was filtered and the filtrate evaporated under the hood. Yellow crystals of tert-butyl-p-benzoquinone were obtained melting at 55°–60° C.

Hexachlorocyclopentadiene, 40 g., and 15.4 g. of tert-butyl-p-benzoquinone were dissolved in 300 ml. of toluene and refluxed for four hours. The solution solidified upon cooling to room temperature. The solid was washed with methanol and recrystallized from benzene. Yellow crystals were obtained, melting at 124°–125° C.

| Calculated | Observed |
|---|---|
| Cl 48.9% | 48.7% |

The product has the following structure:

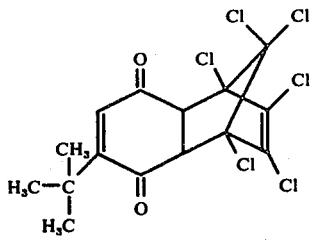

EXAMPLE 9

Reaction product of 1,2,3,4,9,9-hexachloro-1,4,a,8a-tetrahydro-1,4-methanonaphthalene-5,8,-dione and hydroxylamine.

27 g. of 1,2,3,4,9,9-hexachloro-1,4,4a,8a-tetrahydro-1,4-methanonaphthalene-5,8-dione, prepared in accordance with Example 1, and 12 g. of hydroxylamine hydrochloride were dissolved in 200 ml. of dimethylsulfoxide, 5 ml. of water were added and then 13 g. of sodium bicarbonate were added in small increments. The reaction mixture exothermed to 40° C. After one hour, the reaction mixture turned almost white. On pouring this solution into cold water, a pale yellow precipitate was obtained. One recrystallization from methanol gave pale yellow crystals, m.p. 157°–159° C. The infrared spectrum showed no carbonyl and weak absorption at 1610 cm$^{-1}$ which may be assigned as a C=N bond.

The product has the following structure:

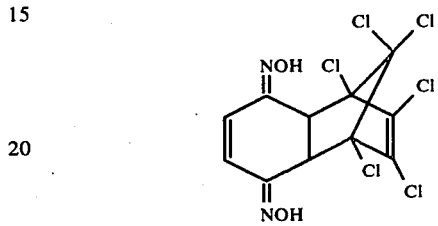

EXAMPLE 10

Preparation of 6-(p-chlorophenylsulfonyl)-1,2,3,4,9,9-hexachloro-1,4-dihydro-1,4-methanonaphthalene-5,8-diol.

38 g. of 1,2,3,4,9,9-hexachloro-1,4-dihydro-1,4-methanonaphthalene-1,8-dione, prepared as in Example 3, were dissolved in 200 ml. of benzene and 20 g. of freshly generated p-chlorobenzenesulfonyl chloride were added. This mixture was refluxed until the orange color disappeared completely (5 hours) and a white precipitate formed. The white solid was filtered off while hot and was recrystallized from benzene yielding white crystals, m.p. 211°–212° C.

| Calculated | Observed |
|---|---|
| Cl 44.6% | Cl 44.8% |
| S 5.7% | S 5.4% |

This reaction was repeated using ethanol rather than benzene as the solvent. An identical product was obtained.

The product has the following structure:

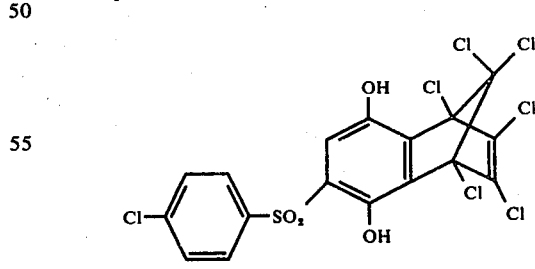

EXAMPLE 11

Preparation of 1,2,3,4,9,9-hexachloro-1,4-dihydro-6-(phenylsulfonyl)-1,4-methanonaphthalene-5,8-diol.

38 g. of 1,2,3,4,9,9-hexachloro-1,4-dihydro-1,4-methanonaphthalene-5,8-dione, prepared as in Example 3, were dissolved in 200 ml. of ethanol and 18 g. of freshly generated benzenesulfonyl chloride were added. This mixture was refluxed for 5 hours and a white precipitate formed. The white solid was filtered off while hot and was recrystallized from benzene yielding white crystals, m.p. 215°–216° C.

| Calculated | Observed |
| --- | --- |
| Cl 42.3% | 42.3% |
| S 6.2% | 6.1% |

The product has the following structure:

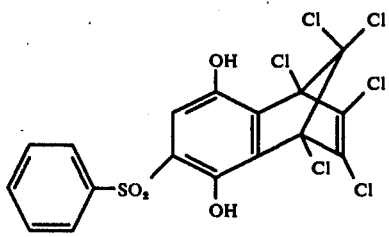

EXAMPLE 12

Preparation of 1,2,3,4,9,9-hexachloro-1,4-dihydro-5,8-dihydroxy-1,4-methanonaphth-6-yl methyl ketone.

76 g. of 1,2,3,4,9,9-hexachloro-1,4-dihydro-1,4-methanonaphthalene-5,8-diol, prepared according to Example 2, were suspended in 100 ml. of acetic acid and then 20 ml. of boron trifluoride-diethyl ether complex were added. This mixture was heated at 100°–105° C for 5 hours. After being cooled to 40° C, the mixture was poured into ice water. After repeated recrystallization from benzene white crystals were obtained, m.p. 135°–140° C.

Nmr showed one aromatic proton at 664 Hz as a singlet, two —OH protons at 601 and 583 Hz as a singlet, and three acetyl protons at 226 Hz as a singlet. Infrared spectrum showed a strong phenolic —OH group and the carbonyl at 1750 cm$^{-1}$.

| Calculated | Observed |
| --- | --- |
| C 36.8% | 35.7% |
| H 1.39 | 1.39 |
| Cl 50.3 | 49.2 |

The product has the following structure:

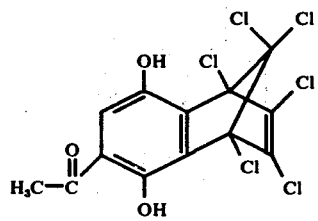

EXAMPLE 13

Preparation of 1,2,3,4,9,9-hexachloro-1,4-dihydro-8-hydroxy-1,4-methanonaphth-5-yl-diethyl phosphate.

19 g. of 1,2,3,4,9,9-hexachloro-1,4-dihydro-1,4-methanonaphthalene-5,8-dione, prepared according to Example 3, and 14 g. of diethylphosphite were mixed and 50 ml. of a methanol solution, which contained 2 g. of CH$_3$ONa, were added slowly under nitrogen atmosphere. An exothermic reaction took place. After completing the addition, the reaction mixture was heated at 80°–90° C for 5 hours and then cooled to room temperature and a slight excess of acetic acid was added to neutralize the base. The reaction mixture was poured into 300 ml. of benzene and washed with water twice and dried over MgSO$_4$. Evaporation of the benzene yielded a brown colored solid. This solid was repeatedly recrystallized from methanol yielding white crystals, m.p. 206°–208° C. The yield was about 30%.

| Calculated | Observed | |
| --- | --- | --- |
| | Test 1 | Test 2 |
| Cl 41.2% | 42.10% | 41.75% |

The product has the following structure:

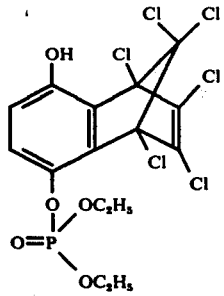

EXAMPLE 14

Preparation of 1,2,3,4,9,9-hexachloro-1,4-dihydro-8-methoxy-1,4-methanonaphth-5-yl-dimethyl phosphate.

20 g. of 1,2,3,4,9,9-hexachloro-1,4-dihydro-1,4-methanonaphthalene-5,8-dione, prepared as in Example 3, were dissolved in 80 ml. of dried benzene and 14 g. of distilled trimethyl- phosphate were added slowly (exothermic) to the solution so that the temperature was maintained at about 50° C. When the addition was completed, the mixture turned dark but then turned yellow after 30 minutes of additional stirring. When benzene solvent was evaporated, a pale yellow solid was obtained. One recrystallization from benzene-Skelly B (50/50) mix-solvent gave white crystals, m.p. 149°–150° C. Infrared showed no hydroxyl or carbonyl group.

Nmr spectrum showed three methoxy protons at 394 Hz and six methoxy protons at 383 Hz. The total yield was about 65%.

| Calculated | Observed |
| --- | --- |
| Cl 42.3% | Cl 42.5% |

| Calculated | Observed |
|---|---|
| P   6.16 | P   6.35 |

The product has the following structure:

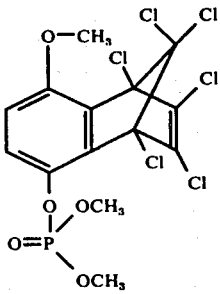

EXAMPLE 15

Preparation of 1,2,3,4,9,9-hexachloro-5,8-diethoxy-1,4-dihydro-1,4-methanonaphthalene.

18 g. of 1,2,3,4,9,9-hexachloro-1,4-dihydro-1,4-methanonaphthalene-5,8-diol, prepared as in Example 2, and 8 g. of NaOH were mixed in 200 ml. of distilled water. The diol dissolved readily, forming the sodium salt. While stirring, an excess of ethylbromide was added and stirring was continued for 24 hours. A white precipitate was filtered off. One recrystallization from methanol resulted in white crystals, m.p. 161°–162° C (yield about 60%). Infrared analysis showed no carbonyl or hydroxyl group.

| Calculated | Observed | |
|---|---|---|
|  | Test 1 | Test 2 |
| Cl   48.9% | 49.3% | 49.0% |

The product has the following structure:

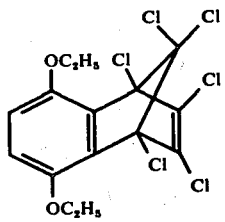

EXAMPLE 16

Preparation of 1,2,3,4,9,9-hexachloro-1,4-dihydro-1,4-methanonaphth-5,8-ylene acetate.

20 g. of 1,2,3,4,9,9-hexachloro-1,4-dihydro-1,4-methanonaphthalene-5,8-diol, prepared as in Example 2, were mixed with 25 g. of acetic anhydride and cooled by a water bath and then one drop of concentrated $H_2SO_4$ was added. The reaction was exothermic and the reaction mixture instantly solidified. One recrystallization from benzene/methanol mixture gave white crystals, m.p. 252°–253° C. The yield was essentially quantitative. Infrared analysis showed ester carbonyl and no hydroxyl group.

| Calculated | Observed | |
|---|---|---|
|  | Test 1 | Test 2 |
| Cl   45.9% | 46.23 | 45.98% |

The product has the following structure:

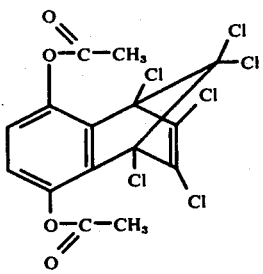

EXAMPLE 17

Preparation of 1,2,3,4,9,9-hexachloro-1,4-dihydro-1,4-methanonaphth-5,8-ylene propionate.

80 g. of 1,2,3,4,9,9-hexachloro-1,4-dihydro-1,4-methanonaphthalene-5,8-diol, prepared in accordance with Example 2, were mixed with 80 g. of propionic anhydride and then a few drops of concentrated $H_2SO_4$ were added. As soon as the $H_2SO_4$ was added the mixture solidified. The thus formed white solid was filtered from excess propionic anhydride on a Buchner funnel and washed twice with water on the funnel. This solid was recrystallized from benzene and white needlelike crystals were obtained, m.p. 204°–205° C. The yield was almost quantitative.

| Calculated | Observed | |
|---|---|---|
|  | Test 1 | Test 2 |
| Cl   43.2% | 42.90 | 42.88% |

The product has the following structure:

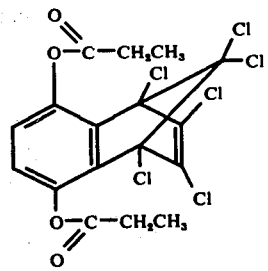

EXAMPLE 18

Preparation of 1,2,3,4,9,9-hexachloro-1,4-dihydro-1,4-methanonaphth-5,8-ylene decanoate.

38 g. of 1,2,3,4,9,9-hexachloro-1,4-dihydro-1,4-methanonaphthalene-5,8-diol, prepared as in Example 2, were dissolved in 150 ml. of dried benzene and 38 g. of decanoyl chloride were added slowly under nitrogen atmosphere. The reaction mixture was heated at 70°–75° C. until HCl evolution ceased. After cooling to room temperature, the benzene was evaporated under vacuum and a liquid product was obtained.

| Calculated | Observed | |
|---|---|---|
| | Test 1 | Test 2 |
| Cl 31.7% | 29.98 | 30.06 |

The product has the following structure:

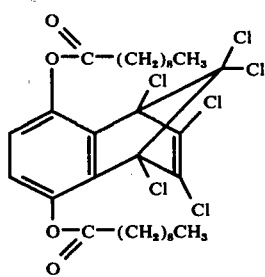

EXAMPLE 19

Preparation of 1,2,3,4,9,9-hexachloro-1,4-dihydro-1,4-methanonaphth-5,8-ylene pivalate.

To a mixture of 38 g. of 1,2,3,4,9,9-hexachloro-1,4-dihydro-1,4-methanonaphthalene-5,8-diol, prepared as in Example 2, and 16 g of pyridine in 200 ml. of dry benzene, 24 g. of pivaloyl chloride were added from a dropping funnel. After four hours heating at 60°–70° C. the mixture was cooled to room temperature and the white pyridinium salt was filtered off. Evaporation of the benzene resulted in a white solid. This solid was recrystallized from benzene-Skelly "B" mixed solvent yielding white crystals, m.p. 134°–135° C.

| Calculated | Observed |
|---|---|
| Cl 38.7% | 38.9% |

The product has the following structure:

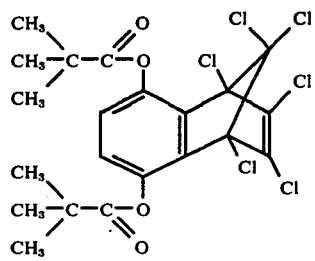

EXAMPLE 20

Preparation of 1,2,3,4,9,9-hexachloro-1,4-dihydro-naphth-5,8-ylene trichloroacetate.

38 g. of 1,2,3,4,9,9-hexachloro-1,4-dihydro-1,4-dimethanonaphthalene-5,8-diol, prepared as in Example 2, 16 g. of pyridine, and 200 ml. of dry benzene were mixed, and 40 g. of trichloroacetylchloride were added slowly to the mixture from a dropping funnel. After four hours heating at 60°–70° C., the mixture was cooled to room temperature and the white pyridinium salt was filtered off. Evaporation of the benzene resulted in a white solid. This solid was recrystallized from benzene-Skelly "B" mixed solvent yielding white crystals, m.p. 135°–136° C. The yield was about 60% after recrystallization. Nmr showed only one singlet at 718 Hz. Infrared showed carbonyl at 1790 cm$^{-1}$ and no —OH group. Chlorine analysis showed:

| Calculated | Observed |
|---|---|
| Cl 63.4% | 61.5% |

The product has the following structure:

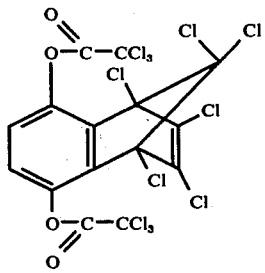

EXAMPLE 21

Preparation of 1,2,3,4,9,9-hexachloro-1,4-dihydro-1,4-methanonaphthalene-5,6,8-triyl acetate.

20 g. of 1,2,3,4,9,9-hexachloro-1,4-dihydro-1,4-methanonaphthalene-5,8-dione, prepared as in Example 3, were mixed with 20 ml. of acetic anhydride, and 3 ml. of concentrated H$_2$SO$_4$ were added to the mixture. The mixture was then stirred vigorously at 90° C. until the orange color disappeared. After cooling to room temperature, the formed white solid was filtered on a Buchner funnel and washed twice with water. This solid was recrystallized from ethanol and white crystals were obtained, m.p. 179°–180° C. Total yield was about 70%. Nmr showed 2 protons (aromatic) at 687.5 Hz, 6 protons (methyl) at 227.5 Hz, and 3 protons (methyl) at 222 Hz. all as singlets. Infrared analysis showed one carbonyl at 1775 cm⁻¹ and no —OH group.

| | Calculated | Observed |
|---|---|---|
| C | 39.0% | 38.8 |
| H | 1.91 | 1.95 |
| Cl | 40.7 | 39.6 |

The product has the following structure:

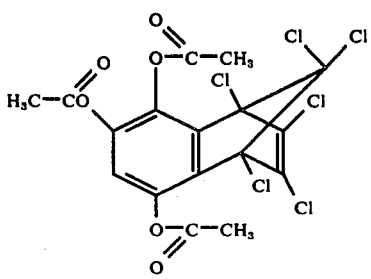

EXAMPLE 22

Preparation of 2,2'-(1,2,3,4,9,9-hexachloro-1,4-dihydro-1,4-methanonapth-5,8-ylenedioxy)diethanol.

NaOH (10g.) was dissolved in 200 ml. of distilled water and then 38 g. of 1,2,3,4,9,9-hexachloro-1,4-dihydro-1,4-methanonaphthalene-5,8-diol, prepared according to Example 2, were added as quickly as possible under nitrogen flow. The diol dissolved readily and then 34 g. (large excess) of chloroethanol were added and the mixture was heated at 50°-60° C. for 12 hours. As the reaction proceeded, a white precipitate formed. This white solid was filtered and washed with water twice. Repeated recrystallization from water-methanol (50/50) mix-solvent gave white crystals, m.p. 150°-151° C. The yield was about 65%.

| | Calculated | Observed | |
|---|---|---|---|
| | | Test 1 | Test 2 |
| C | 38.4% | 38.5 | 38.7% |
| H | 2.6 | 2.59 | 2.68 |
| Cl | 45.4 | 44.8 | 44.5 |

The product has the following structure:

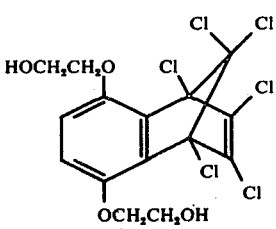

EXAMPLE 23

Preparation of 5,8-diallyloxy-1,2,3,4,9,9-hexachloro-1,4-dihydro-1,4-methanonaphthalene.

NaOH (20 g.) was dissolved in 300 ml. of water-methanol mix solvent (200/100) and nitrogen was bubbled through the solution for 20 minutes. 80 g. of 1,2,3,4,9,9-hexachloro-1,4-dihydro-1,4-methanonaphthalene-4,8-diol, prepared as in Example 2, were quickly added under nitrogen flow. While stirring, 40 g. of allylbromide were added at one time. A slight exothermic reaction was observed. This reaction mixture was heated at 50°-60° for 6 hours. When cooled in an ice water bath, a dark colored solid was obtained. Repeated recrystallization from methanol gave white crystals, m.p. 114°-115° C. The yield after the recrystallization was poor (about 30%). Nmr showed two aromatic protons at 677 Hz as a singlet, six olefinic protons at 615-519 Hz as a complicated multiplet, and four methylene protons at 452.2 - 447.5 Hz as a multiplet. Infrared analysis showed no —OH group.

| Elemental Analysis: | Calculated | Observed |
|---|---|---|
| Carbon | 44.2% | 43.6% |
| Hydrogen | 2.6 | 2.5 |
| Chlorine | 46.2 | 45.5 |

The product has the following structure:

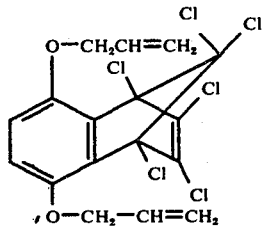

EXAMPLE 24

Preparation of 1,2,3,4,9,9-heptachloro-1,4,4a8a-tetrahydro-1,4-methanonaphthalene-5,8-dione.

A mixture of 272.8 grams (1 mol) of hexachlorocyclopentadiene, 142.5 grams (1 mol.) of 2-chloro-1,4-benzoquinone and 35 ml. of toluene was stirred continuously and gradually heated to 130°-140° C. during a period of two hours. This temperature was maintained for five hours. The brown solution crystallized while at room temperature overnight. The crude product was recyrstallized from a mixture of 3 liters of Skellysolve and 0.5 liter of acetone. The recrystallized product was a reddish-orange, coarsely crystalline solid. The yield was 342.6 grams (82.5% of theory). M.P. 175°-177° C. The product has the following structure:

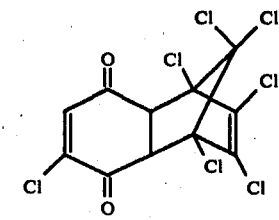

EXAMPLE 25

Preparation of 1,2,3,4,6,9,9-heptachloro-1,4-dihydro-1,4-methanonaphthalene-5,8-diol. Skellysolve. recrystallized 12.5°

A mixture of 256 grams (0.62 mol.) of 1,2,3,4,6,9,9-heptachloro-1,4,4a,8a-tetrahydro-1,4-methanonaphthalene-5,8-dione, prepared according to Example 24, and 500 ml. of methanol in a 2 liter reaction flask was stirred at room temperature while air in the reaction vessel was swept out with nitrogen. Six ml. of pyridine was then added to the liquid-solid mixture. The resulting reaction mixture was continuously stirred, and refluxed vigorously for 8.5 hours. After cooling the mixture to 0° C., it was filtered, and the crude solid was washed with cold Skellysolve. Yield 121 grams. The product was recrystallized from a mixture of 1000 ml. of Skellysolve and 250 ml. of acetone. M.P. 120.5° – 122° C. The product has the following structure:

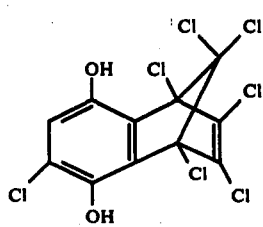

EXAMPLE 26

Preparation of 1,2,3,4,6,9,9-heptachloro-1,4-dihydro-1,4-methanonaphth-5,8-ylene acetate.

23 g. of 1,2,3,4,6,9,9,-heptachloro-1,4-dihydro-1,4-methanonaphthalene-5,8-diol, prepared as in Example 25, were mixed with 25 g. of acetic anhydride. The mixture was cooled in a water bath and then one drop of concentrated $H_2SO_4$ was added. The reaction was exothermic and the reaction mixture instantly solidified. Recrystallization from benzene/methanol solvent gave white crystals, m.p. 160°–162° C. The yield was essentially quantitative.

| Calculated | Observed |
|---|---|
| Cl 49.6% | 49.1% |

The product has the following structure:

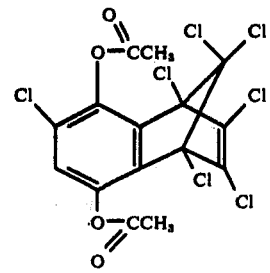

EXAMPLE 27

Preparation of 6-(p-chlorobenzenesulfonyl)-1,2,3,4,9,9-hexachloro-1,4-dihydro-1,4-methanonaphth-5,8-ylene acetate.

30 g. of 6-(p-chlorobenzenesulfonyl)-1,2,3,4,9,9-hexachloro-1,4-dihydro-1,4-methanonaphthalene-5,8-diol, prepared as in Example 10, were mixed with 40 ml. of acetic anhydride and a few drops of concentrated $H_2SO_4$ were added. As soon as the $H_2SO_4$ was added the reaction became exothermic and the reaction mixture solidified. After adding 10 ml. more of acetic anhydride and shaking for 10 more minutes the white solid was filtered off on a Buchner funnel. This solid was recrystallized from benzene-Skelly B mixed solvent yielding white crystals, m.p. 215°–216° C.

| Calculated | Observed | |
|---|---|---|
|  | Test 1 | Test 2 |
| Cl 38.7% | 38.54 | 38.78% |
| S 5.0 | 4.46 | 4.58 |

The product has the following structure:

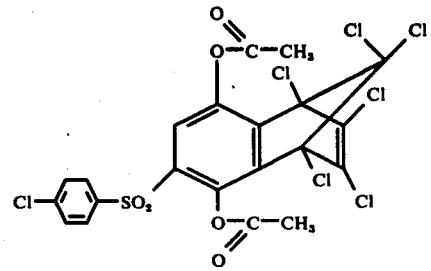

EXAMPLE 28

Preparation of 1,2,3,4,9,9-hexachloro-1,4-dihydro-1,4-methanonaphth-5,8-ylene butylcarbamate.

38 g. of 1,2,3,4,9,9-hexachloro-1,4-dihydro-1,4-methanonaphthalene-5,8-diol, prepared as in Example 2, were dissolved in 200 ml. of dry benzene and 25 g. of n-butylisocyanate and then a few drops of triethylamine were added. The reaction mixture was then heated at 70°–75° C. for 3 hours. After cooling to room temperature, a white precipitate was formed and was filtered off on a Buchner funnel. This white solid was insoluble in benzene and melted at 201°–202° C.

| Calculated | Observed |
|---|---|
| Cl 36.8% | 37.4% |
| N 4.8 | 4.7 |

The product has the following structure:

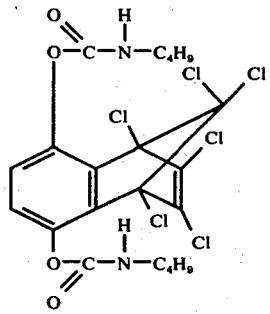

EXAMPLE 29

Preparation of
1,2,3,4,9,9-hexachloro-1,4-dihydro-1,4-methanonaphth-5,8-ylene diethyl carbonate.

38 g. of 1,2,3,4,9,9-hexachloro-1,4-dihydro-1,4-methanonaphthalene-5,8-diol, prepared as in Example 2, were dissolved in a mixture of 200 ml. of dry benzene and 16 g. of pyridine. Then 25 g. of chloroethyl carbonate were added slowly. An exothermic reaction ensued. This reaction mixture was heated under gentle reflux of benzene. After 6 hours the reaction mixture was cooled to room temperature and the pyridinium salt formed was filtered off. Evaporation of benzene resulted in a white solid. This solid was recrystallized from hexane-benzene mixed solvent and yielded white crystals, m.p. 116°-117° C.

| Calculated | Observed |
|---|---|
| Cl 40.6% | 39.9% |

The product had the following structure:

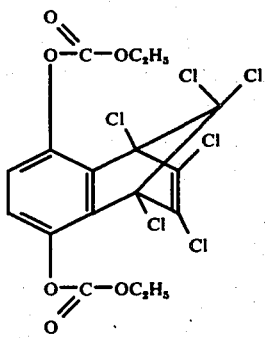

EXAMPLE 30

Preparation of
1,2,3,4,9,9-hexachloro-1,4-dihydro-8-hydroxy-1,4-methanonaphth-5-yl p-chlorophenylsulfonate.

38 g. of 1,2,3,4,9,9-hexachloro-1,4-dihydro-1,4-dihydro-1,4-methanonaphthalene-5,8-dione, prepared as in Example 3, were dissolved in 200 ml. of benzene and 20 g. of freshly generated p-chlorobenzenesulfinyl chloride was added. This mixture was refluxed until the orange color disappeared completely (5 hours) and a white precipitate formed. The white solid was filtered off. (See Example 10). The filtrate solution was concentrated and dissolved in benzene-Skelly B (50/50) mixed solvent and treated with charcoal. Evaporation of the solvent gave a white solid. This solid was recrystallized from Skelly B-benzene (50/50) solvent yielding white crystals, m.p. 165° C.

| Calculated | Observed |
|---|---|
| Cl 44.6% | Cl 44.4% |
| S 5.7 | S 5.6 |

The product has the following structure:

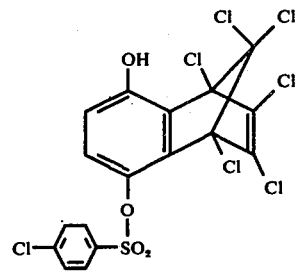

EXAMPLE 31

Preparation of
1,2,3,4,9,9-hexabromo-1,4-dihydro-1,4-methanonaphthalene-5,8-diol.

Distilled water (3.34 kg.) was placed in a 5 liter, 3-neck, round bottom flask equipped with a stirrer, condenser, thermometer, and cooling bath. Sodium hydroxide (528 g.; 13.2 moles; 100% excess) was added to the water in portions, and the solution was stirred continuously. When the addition was completed and the temperature of the solution was at 0° C. or slightly lower, bromine (527.4 g.; 3.3 moles; 169 ml.) was added in a fairly rapid stream through a dropping funnel. The temperature of the solution was kept at or somewhat below 0° C. during this addition of bromine. When the addition was completed and the temperature of the hypobromite solution was −2° to −7° C., a (−15° to −5° C.) solution of cold, freshly-distilled 1,3cyclopentadiene (33.05 g.; 0.5 mole; 41.07 ml.) in 400 ml. of Skellysolve was added rapidly over a period of about 5 minutes to the continuously stirred sodium hypobromite solution. When this addition was completed, stirring was continued and the reaction mixture was allowed to warm to about 10° C. The mixture was transferred to a six liter separatory funnel and the layers were separated. The aqueous layer was extracted at once with three 500 ml. portions of Skellysolve and the combined extracts were added to the Original Skellysolve solution. The resulting solution was thoroughly dried over molecular sieves, filtered, and the filtrate was placed on a steam bath to evaporate solvents. The residual, unrecrystallized 1,2,3,4,5,5-hexabromo-1,3-cyclopentadiene (237.3 g.; 88% yield), after recrystallization from cyclohexane, melted at 87°–88° C.

A mixture of benzoquinone, 10.8 g. toluene (40 ml) and 1,2,3,4,5,5-hexabromo-1,3-cyclopentadiene (60 g.) was heated to reflux temperature and refluxed for four hours. At the end of this reaction period a dark solid had formed. This solid was placed on a Buchner funnel and washed with Skelly B solvent and a small amount of methanol. The solid was then recrystallized from benzene and white crystals were obtained, m.p. 204°–206° C.

The product has the following structure:

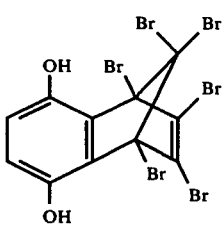

EXAMPLE 32

Preparation of 1,2,3,4,9,9-hexabromo-1,4-dihydro-1,4-methanonaphth-5,8-ylene acetate.

10 g. of 1,2,3,4,9,9-hexabromo-1,4-dihydro-1,4-methanonaphthalene-5,8-diol, prepared according to Example 31 were mixed with 20 ml. of acetic anhydride and one drop of concentrated H$_2$SO$_4$ was added to the mixture. An exothermic reaction ensued. This reaction mixture was stirred for 30 minutes and then poured into ice water. The thus formed white solid was filtered off and recrystallized from benzene yielding white needle crystals, m.p. 304°–305° C.

| Calculated | Observed | |
|---|---|---|
| | Test 1 | Test 2 |
| Br 66.9% | 65.70 | 65.21% |

The product has the following structure:

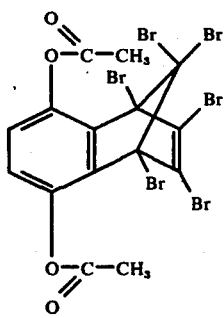

EXAMPLE 33

Preparation of (1,2,3,4,9,9-hexachloro-1,4-dihydro-1,4-methanonaphth-5,8-ylenedioxy) diacetic acid.

76 g. of 1,2,3,4,9,9-hexachloro-1,4-dihydro-1,4-methanonaphthalene-5,8-diol prepared as in Example 2 were dissolved in a NaOH/H$_2$O solution (16 g/250 ml.) and then 0.4 moles of sodium-α-chloroacetate solution (46.6 g/100 ml H$_2$O) was added slowly under a dry nitrogen atmosphere. This mixture was heated at 80°–90° C. for 6 hours and then cooled to room temperature and acidified with dilute HCl solution. The precipitated brown colored solid was repeatedly recrystallized from water-methanol mixed solvent.

The product has the following structure:

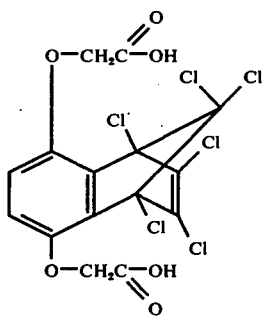

EXAMPLE 34

Preparation of 1,2,3,4,9,9-hexachloro-1,4-dihydro-1,4-methanonaphth-5,8-ylene benzoate.

38 g. of 1,2,3,4,9,9-hexachloro-1,4-dihydro-1,4-methanonaphthalene-5,8-diol prepared as in Example 2, 16 g. of pyridine, and 200 ml. of dry benzene were mixed and 28 g. of benzoyl chloride were added slowly to the mixture from a dropping funnel. After four hours heating at 60°–70° C., the mixture was cooled to room temperature and the white pyridinium salt was filtered off. Evaporation of the benzene resulted in a white solid. This solid was recrystallized from benzene-Skelly B mixed solvent yielding white crystals, m.p. 213°–215° C. The yield was about 60% after recrystallization.

The product has the following structure:

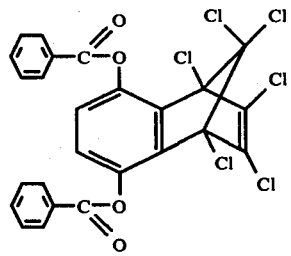

EXAMPLE 35

Preparation of 1,2,3,4,9,9-hexachloro-1,4-hydro-1,4-methanonaphth-5,8-ylene methanesulfonate.

38 g. of 1,2,3,4,9,9-hexachloro-1,4-dihydro-1,4-methanonaphthalene-5,8-diol prepared as in Example 2 and 16 g. of pyridine were dissolved in 300 ml. of dry benzene and 22 g. of methylsulfonic chloride was added slowly from a dropping funnel. After refluxing for 5 hours the mixture was cooled to −10° C. and the pyridinium salt was filtered off. The solution was washed twice with water and dried over anhydrous magnesium sulfate. Evaporation of benzene yielded a crude solid. This solid was recrystallized twice from ethanol and white crystals were obtained, m.p. 184°–186° C.

| Calculated | Observed | |
|---|---|---|
| | Test 1 | Test 2 |
| Cl 39.7% | 38.76 | 38.45 |

The product has the following structure:

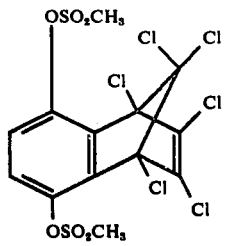

EXAMPLE 36

Preparation of 6-tert-butyl-1,2,3,4,9,9-hexachloro-1,4-dihydro-1,4-methanonaphthalene-5,8-diol.

10 g. of 6-tert-butyl-1,2,3,4,9,9-hexachloro-1,4,4a,-8a-tetrahydro-1,4-methanonaphthalene-5,8-dione, prepared according to Example 8, were dissolved in 50 ml. of methanol. A few drops of pyridine were added and the solution was refluxed strongly for three hours. Evaporation of the methanol yielded an oily material which upon recrystallization twice from Skelly B gave white needle crystals melting at 96°–98° C.

Nmr showed nine tert.-butyl protons at 134 Hz as a singlet, two hydroxyl protons at 347 Hz and one aromatic proton at 669 Hz. Infrared spectrum showed strong phenolic -OH group absorption at 3500 cm$^{-1}$ and no carbonyl. The product has the following structure:

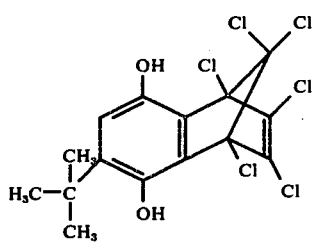

EXAMPLE 37

Preparation of 0,0' 1,2,3,4,9,9-hexachloro-1,4-dihydro-1,4-methanonaphth-5,8-ylene dimethylthiocarbamate.

38 g. of 1,2,3,4,9,9-hexachloro-1,4-dihydro-1,4-methanonaphthalene-5,8-diol, prepared as in Example 2, and 11 g. of triethylamine were dissolved in 300 ml. of dry benzene and 25 g. of dimethylthiocarbamoyl chloride were added slowly to the solution. After refluxing strongly for six hours the reaction mixture was cooled to room temperature and the salt was filtered off. The benzene solution was washed twice with water and then dried over anhydrous magnesium sulfate. Evaporation of the benzene yielded the crude solid. This solid was recrystallized from benzene and pale yellow crystals were obtained, m.p. 195°–198° C.

The product has the following structure:

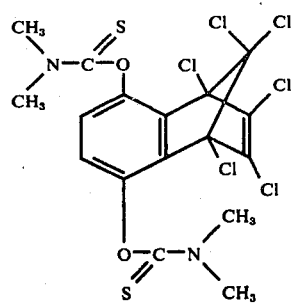

EXAMPLE 38

Preparation of 1,2,3,4,9,9-hexachloro-1,4-dihydro-1,4-methanonaphth-5,8-ylene bis(ethylene phosphite).

38 g. of 1,2,3,4,9,9-hexachloro-1,4-dihydro-1,4-methanonaphthalene-5,8-diol, prepared as in Example 2, were dissolved in 300 ml. of dry benzene and 26 g. of freshly distilled chloroethylene phosphite were added slowly from a dropping funnel. The reaction mixture was refluxed until no more HCl evolved (six hours). The solvent was evaporated completely under vacuum and a pale yellow waxy material was obtained. Purification was difficult due to the hydrolytic nature of the compound.

The product has the following structure:

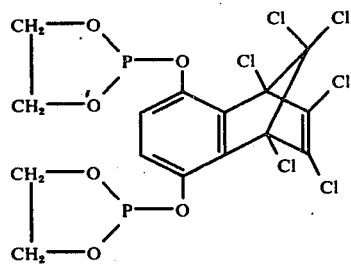

EXAMPLE 39

Preparation of 1,2,3,4,9,9-hexachloro-1,4-dihydro-1,4-methanonaphth-5,8-ylene o,o'-hydroxybenzoate.

A mixture of 1,2,3,4,9,9-hexachloro-1,4-dihydro-1,4-methanonaphthalene-5,8-diol prepared according to Example 2 (10.0g.), salicyclic acid (7.4 g.), and phosphorus pentachloride (3.6 g.), was heated in refluxing xylene for two days. The crystals which formed upon cooling the reaction mixture were separated by filtration. The crude product was recrystallized from benzenepetroleum ether to give a pure sample, m.p. 232°–233° C. Additional product was obtained by removal of the solvent and recrystallization of the residue from benzene-petroleum ether. Total yield was about 27%.

| Calculated | | Observed | |
|---|---|---|---|
| | | Test 1 | Test 2 |
| C | 48.3% | 48.40 | 48.42% |
| H | 1.94 | 2.14 | 2.29 |

The compound has the following structure:

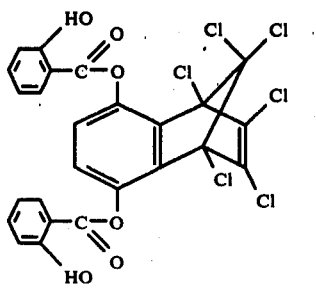

EXAMPLE 40

Preparation of 1,2,3,4,9,9-hexachloro-1,4,4a,6,7,8a-hexahydro-1,4-methanonaphthalene-5,8-dione.

38 g. of 1,2,3,4,9,9-hexachloro-1,4,4a,8a-tetrahydro-1,4-methanonaphthalene-5,8-dione, prepared as in Example 1, were suspended in 150 ml. of glacial acetic acid and then this mixture was poured into 20 g. of zinc dust suspended in 150 ml. of distilled water. A slight exotherm occurred during stirring and the temperature was maintained at 50° C. for 3 hours by external heating. Then 200 ml. of chloroform were added and stirring was continued for 30 minutes more. The chloroform layer was separated and washed with a saturated sodium carbonate solution and dried over anhydrous magnesium sulfate. Evaporation of the chloroform left a white solid. One recrystallization from methanol gave white crystals, m.p. 169°–170° C. Infrared spectrum showed carbonyl at 1740 cm$^{-1}$. The nmr indicated two bridgehead protons at 431 Hz (singlet) and four α-protons at 303 Hz and 245 Hz (as a multiplet).

| Calculated | | Observed | |
|---|---|---|---|
| | | Test 1 | Test 2 |
| C | 34.5% | 35.30 | 35.26 |
| H | 1.6 | 1.63 | 1.79 |
| Cl | 55.6 | 54.89 | 54.36 |

The product has the following structure:

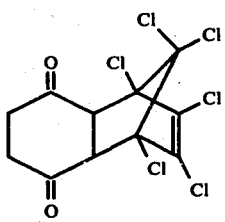

EXAMPLE 41

Preparation of 1,2,3,4,9,9-hexachloro-1,4,4a,6,7,8a-hexahydro-6-phenylsulfonyl-1,4-methanonaphthalene-5,8-dione.

38 g. of 1,2,3,4,9,9-hexachloro-1,4,4a,8a-tetrahydro-1,4-methanonaphthalene-5,8-dione, prepared as in Example 1, were dissolved in 250 ml. of benzene, 15 g. of freshly generated benzene sulfinic acid were added and then a few drops of water were added. This reaction mixture was heated at 40°–45° C. for 12 hours and then the benzene was evaporated. The white solid residue obtained was recrystallized from benzene twice and yielded white crystals, m.p. 157°–158° C. The yield was about 88%.

| Calculated | | Observed | |
|---|---|---|---|
| | | Test 1 | Test 2 |
| Cl | 40.9% | 39.11 | 39.63% |
| S | 6.1 | 5.74 | 5.80 |

The product has the following structure:

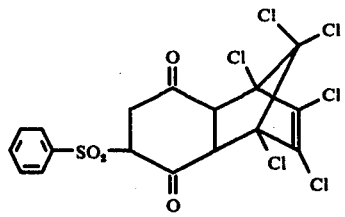

EXAMPLE 42

Preparation of 6-butylthio-1,2,3,4,9,9-hexachloro-1,4,4a,6,7,8a-hexahydro-1,4-methanonaphthalene-5,8-dione.

20 g. of 1,2,3,4,9,9-hexachloro-1,4,4a,8a-tetrahydro-1,4-methanonaphthalene-5,8-dione, prepared as in Example 1, were dissolved in 60 ml. of benzene and then 10 g. of n-butylmercaptan and a few crystals of ferric chloride were added. This reaction mixture was shaken for 24 hours (Parr shaker). When the benzene was evaporated a white solid was obtained. One recrystallization from benzene-Skelly B mixture yielded white crystals, m.p. 97°–98° C. The infrared spectrum showed strong carbonyl at 1750 cm$^{-1}$.

| Calculated | | Observed | |
|---|---|---|---|
| | | Test 1 | Test 2 |
| Cl | 45.2% | 44.84 | 44.52 |

The product has the following structure:

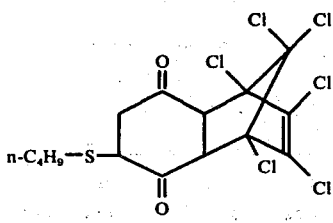

EXAMPLE 43

Preparation of
1,2,3,4,9,9-hexachloro-6,7-epoxy-1,4,4a,6,7,8a-hexahydro-1,4-methanonaphthalene-5,8-dione.

38 g. of 1,2,3,4,9,9-hexachloro-1,4,4a,8a-tetrahydro-1,4-methanonaphthalene-5,8-dione, prepared according to Example 1, were added slowly to a solution of 200 ml. of ethanol containing 20 ml. of 30% hydrogen peroxide and 13 g. of sodium carbonate at such a rate that the temperature was maintained at 40°–50° C. The yellow color of the dione disappeared quickly. The solution was then cooled to 10°–13° C. and a white precipitate formed. This solid was filtered and recrystallized from ethanol, m.p. 180°–181° C.

|  | Calculated | Observed |
|---|---|---|
| C | 33.2% | 32.8% |
| H | 1.0 | 1.15 |
| Cl | 53.7 | 52.75 |

The product has the following structure:

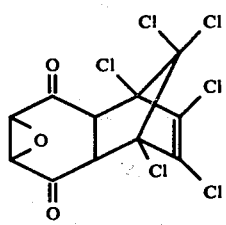

EXAMPLE 44

Preparation of
1,2,3,4,9,9-hexachloro-1,4,4a,5,6,7,8,8a-octahydro-1,4-methanonaphthalene-5,8-diol.

38 g. of 1,2,3,4,9,9-hexachloro-1,4,4a,8a-tetrahydro-1,4-dimethanonaphthalene-5,8-dione, prepared as in Example 1, were dissolved in 200 ml. of ethanol and about 20% excess NaBH₄ was added over a 30 minute period in small amounts so that the temperature was maintained below 50° C. The ethanol was then evaporated under vacuum and the residue was chromatographed on alumina using benzene as solvent. Evaporation of the benzene yielded a white solid. Fractional crystallization from benzene-hexane (50/50) solvent yielded as the major product a white solid melting at 163°–168° C. Nmr and infrared spectra indicate a major part is completely reduced product, and a minor part is only carbonyl reduced product.

The product has the following structure:

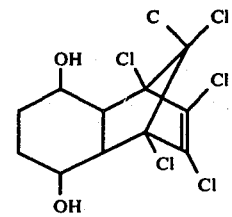

EXAMPLE 45

Preparation of
1,2,3,4,9,9-hexachloro-1,4,4a,8a-tetrahydro-6-methyl-1,4-methanonaphthalene-5,8-dione.

To a mixture of methyl-p-benzoquinone (60 g.), and hexachlorocyclopentadiene (140 g.), was added 20 ml. of toluene. This reaction mixture was then heated at 130°–140° C. for 3 hours. Upon cooling to room temperature the mixture solidified. This solid was washed with Skelly "B" solvent several times on a Buchner funnel and recrystallized from a Skelly "B"-benzene mixed solvent (20/80). Pale yellow crystals were obtained, m.p. 163°–165° C.

The product has the following structure:

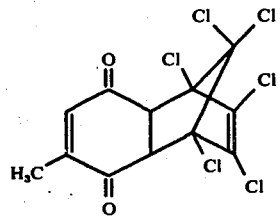

EXAMPLE 46

Preparation of
1,2,3,4,12,12-hexachloro-1,4,4a,5,8,8a,9a,10a-octahydro-1,4:5,8-dimethanoanthracene-9,10-dione.

190 g. of the dione prepared according to Example 1 were dissolved in 800 ml. of acetone and 45 g. of freshly generated cyclopentadiene were added slowly at room temperature. A white precipitate formed when approximately one-third of the cyclopentadiene had been added. The reaction mixture was stirred for two hours after all the cyclopentadiene had been added. The white solid was filtered off and additional precipitation occurred when the filtrate was concentrated. The combined yield was almost quantitative. The solid was recrystallized from benzene/Skelly B (50/50) yielding needle like crystals, m.p. 196°–198° C. Infrared spectrum showed a carbonyl at 1710 cm⁻¹ and nmr agreed with the proposed structure.

| Calculated | Observed | |
|---|---|---|
|  | Test 1 | Test 2 |
| Cl 47.75% | 47.24% | 46.78 |

The product has the following structure:

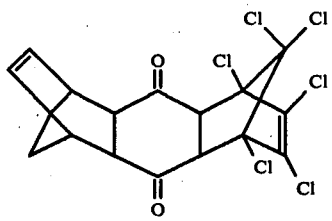

EXAMPLE 47

Preparation of
1,2,3,4,11,11-hexachloro-1,4,4a,9a-tetrahydro-1,4-methanoanthracene-9,10-dione.

Hexachlorocyclopentadiene (60 g.), 1,4-naphthoquinone (31.6 g.), and 30 ml. of toluene were mixed, heated to reflux temperature, and maintained at this temperature for 4 hours. After cooling to room temperature and extracting the excess hexachlorocyclopentadiene with Skelly "B" solvent, the mixture solidified slowly. This crude brown solid was recrystallized repeatedly from benzene/Skelly "B" mix-solvent (70/30) to yield white crystals, m.p. 116°–118° C.

The product has the following structure:

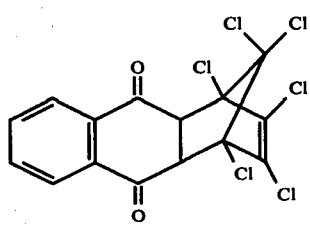

EXAMPLE 48

Preparation of
1,2,3,4,9,9-hexachloro-1,4-dihydro-6-methyl-1,4-methanoaphthalene-5,8-diol.

30 g. of 1,2,3,4,9,9-hexachloro-1,4,4a,8a-tetrahydro-6-methyl-1,4-methanonaphthalene-5,8-dione, prepared according to Example 45, were suspended in 150 ml. of methanol. 2 ml. of pyridine were added and the mixture was refluxed for 4 hours. Upon cooling in an ice-water bath, a crude white solid formed. This solid was recrystallized from methanol and white crystals were obtained, m.p. 159°–161° C.

The product has the following structure:

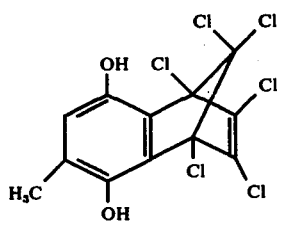

EXAMPLE 49

Preparation of
1,2,3,4,12,12-hexachloro-1,4,4a,5,6,7,8,8a,9a,10a decahydro-1,4:5,8-dimethanoanthracene-9,10-dione.

22.5 g. of 1,2,3,4,12,12-hexachloro-1,4,4a,5,8,8a,9a,10a-octahydro-1,4:5,8-dimethanoanthracene-9,10-dione, prepared as in Example 46, were dissolved in 300 ml. of ethanol and 0.5 g. of Pd-C was added and shaken under 20 lbs. of hydrogen pressure on a Parr Shaker. 5 lbs. of hydrogen were absorbed within 30 minutes. The reaction mixture was filtered and upon evaporation of the ethanol a white solid was obtained. One recrystallization from benzene/Skelly B (50/50) solvent mix gave white crystals, m.p. 190°–192° C. Infrared spectrum and nmr showed good agreement with the proposed structure.

| Calculated | Observed | |
|---|---|---|
|  | Test 1 | Test 2 |
| Cl 47.4% | 47.29% | 47.38% |

The product has the following structure:

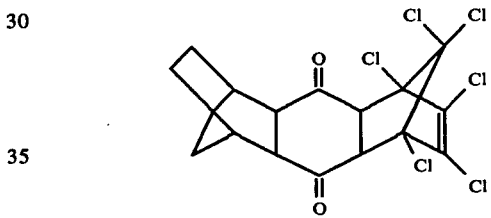

EXAMPLE 50

Preparation of
1,2,3,4,11,11-hexachloro-1,4,4a,5,8,8a,9a,10a-octahydro-1,4-methano-cis(10a,8a)-anthracene-9,10-dione.

40 g. of 1,2,3,4,9,9-hexachloro-1,4,4a,8a-tetrahydro-1,4-methanonaphthalene-5,8-dione, prepared as in Example 1, 200 ml. of acetone and 60 g. of 1,3-butadiene were charged in an autoclave and heated at 60°–70° C for 24 hours. The reaction mixture was then cooled to room temperature and the acetone was removed by a rotary evaporator. The white solid thus obtained was recrystallized from benzene/Skelly B (50/50) solvent mix and white crystals were obtained, m.p. 185°–187° C. By further condensing the supernatant liquid, lower melting white crystals were obtained, m.p. 138°–140° C. Nmr spectra showed the higher melting solid to be the cis compound and the lower melting solid to be the trans compound.

| Calculated | Observed | |
|---|---|---|
|  | Test 1 | Test 2 |
| Cl 49.08% | 47.89% | 47.66% |

The product has the following structure:

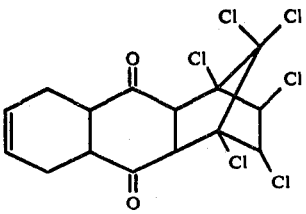

EXAMPLE 51

Preparation of
1,2,3,4,5,7,12,12-octachloro-1,4,4a,5,6,7,8,8a,9a,10a-decahydro-1,4:5,8-dimethanoanthracene-9,10-dione.

45 g. of 1,2,3,4,12,12-hexachloro-1,4,4a,5,8,8a,9a,10a-octahydro-1,4:4,8-dimethanoanthracene-9,10-dione, prepared as in Example 46, were dissolved in 300 ml. of carbon tetrachloride and chlorine gas was bubbled through the solution until all solid dissolved. A white solid was obtained by evaporation of the carbon tetrachloride. Recrystallization from benzene/Skelly B (50/50) yielded a pure product melting at 219°–221° C. Infrared spectrum and nmr showed agreement with the proposed structure.

| Calculated | Observed | |
|---|---|---|
|  | Test 1 | Test 2 |
| Cl 54.9% | 54.04% | 54.13% |

The product has the following structure:

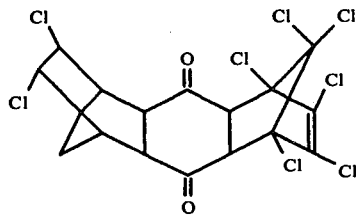

EXAMPLE 52

2,3,4,5-Tetrachlorocyclopentadienone dimethyl acetal.

Hexachlorocyclopentadiene (818.4 g.; 3.0 moles) and methanol (500 ml.) were placed in a 3 liter, round bottom, 3-neck flask equipped with stirrer, condenser, thermometer, dropping funnel and heating mantle. The mixture was stirred continuously while a solution of potassium hydroxide (345.1 g.; 6.15 moles) in methanol (800 ml.) was added in a moderate stream during one hour. The temperature of the reaction mixture was maintained at 30°–38° C. by external cooling of the flask when required. After all the potassium hydroxide solution had been added the temperature of the mixture was maintained at 33°–35° C. by very gently heating for 90 minutes. The reaction mixture was then filtered, and the filtrate was brought to pH 7 by the addition of conc. hydrochloric acid (12.0 ml.). Solvent was evaporated from the neutral solution and the concentrated filtrate was mixed with twice its volume of water, and extracted with Skellysolve three times. The combined extract was dried over molecular sieves, filtered, and freed of solvent. Distillation of the residual liquid under reduced pressure gave 2,3,4,5-tetrachlorocyclopentadienone dimethyl acetal (522 g.; B.P. 65.5° C./0.46 mm.).

The product has the following structure:

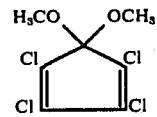

EXAMPLE 53

Preparation of
1,2,3,4-tetrachloro-1,4,4a,8a-tetrahydro-6,8a-dimethyl-1,4-methanonaphthalene-5,8,9-trione-9-dimethyl.acetal.

2,5-dimethoxy-p-benzoquinone (25 g.), and 52 g. (excess) of 2,3,4,5-tetrachlorocyclopentadienone-dimethyl acetal prepared according to Example 52 were dissolved in 40 ml. of o-dichlorobenzene and refluxed overnight. After cooling to room temperature a brown solid formed. This solid was washed with Skelly/B on a Buchner funnel and then recrystallized from benzene. The thus obtained yellow solid melted at 128°–130° C. The yield was about 41%.

The product has the following structure:

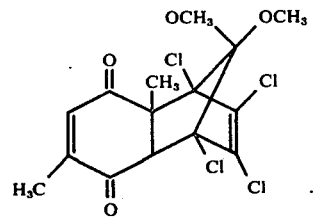

EXAMPLE 54

Preparation of
5,6,7,8,9,9-hexachloro-2,3,4a,5,8,8a-hexahydro-5,8-methanonaphthal-2,3-azine-1,4-dione.

Chlorendic anhydride (37 g.) was dissolved in 150 ml. of ethanol and 10 g. of hydrazine and then 10 ml. of acetic acid were added. The mixture was heated at 80°–85° C. for 4 hours and cooled to room temperature. The white solid that formed was filtered off and recrystallized from ethanol, m.p. 175°–176° C.

The product has the following structure:

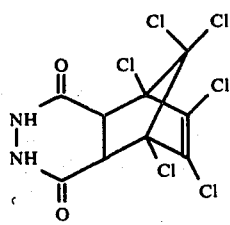

EXAMPLE 55

1,2,3,4-Tetrachloro-1,4,4a,8a-tetrahydro-1,4-methanonaphthalene-5,8,9-trione 9-dimethyl acetal.

A mixture of 2,3,4,5-tetrachlorocyclopentadienone dimethyl acetal (263.9 g.; 1.0 mole), prepared according to Example 52, p-benzoquinone (108.1 g.; 1.0 mole) and toluene (35.0 ml.) in a 3 liter, 3-neck, round bottom flask equipped with a stirrer, condenser, thermometer and heating mantle was stirred continuously and heated to maintain vigorous refluxing for a period of 7 hours. The reaction mixture was removed from the flask while still liquid, and allowed to crystallize. The solid was slurried with cold methanol (2.0 liters), and the slurry was filtered. The washed solid was dissolved in 5.5 liters of hot methanol, treated with Darco decolorizing charcoal, filtered, and crystallized. The yield of lemon-yellow, 1,2,3,4-tetrachloro-1,4,4a,8a-tetrahydro-1,4-methanonaphthalene-5,8,9-trione 9-dimethyl acetal was 205 g.; M.P. 162°–163° C.

The product has the following structure:

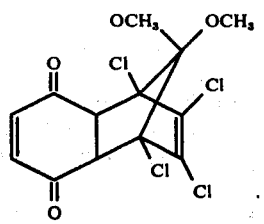

EXAMPLE 56

Preparation of 1,2,3,4-tetrachloro-1,4-dihydro-5,8-dihydroxy-1,4-methanonaphthalene-9-one dimethyl acetal.

Five hundred milliliters of methanol and 74.4 grams (0.2 mol) of 1,2,3,4-tetrachloro-1,4,4a,8a-tetrahydro-1,4-methanonaphthalene-5,8,9-trione 9-dimethyl acetal, prepared according to Example 55, were placed in a reaction flask and the air in the flask was then swept out with nitrogen. Two milliliters of pyridine were added to the reaction mixture, which was then stirred continuously and heated sufficiently to cause vigorous refluxing. Stirring and refluxing were maintained for 5 ½ hours. The reaction mixture was cooled in ice water for a short time and then filtered. The solid was protected from light while being air-dried on the funnel. An additional small amount of product was obtained from the filtrate by cooling it for a short time in dry ice and filtering. The total yield of white, finely crystalline 1,2,3,4-tetrachloro-1,4-dihydro-5,8-dihydroxy-1,4-methanonaphthalene-9-one dimethyl acetal was 66.7 grams (90% of theory). M.P. 203°–204° C.

The product has the following structure:

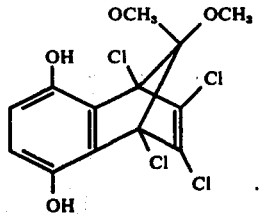

EXAMPLE 57

Preparation of endo-4a,6,7,8a-tetrachloro-1,4,4a,5,8,8a-hexahydro-1,4-methanonaphthalene-5,8-dione.

A mixture of 123 g. of chloranil, 37 g. of cyclopentadiene, 1 ml. of a 50% triethylamine-methanol solution, and 400 ml. of benzene was placed in a polymerization bottle, and the bottle was capped and placed in a bath heated at 65° C. for 72 hours. The adduct was isolated and purified by recrystallization from methanol, followed by sublimation below 100° at 1 mm. The pure adduct had a melting point of 145°–146° C.

The product has the following structure:

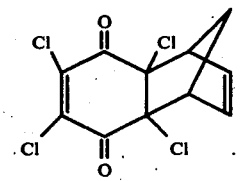

EXAMPLE 58

Preparation of 1,2,3,4-tetrachloro-1,4-dihydro-9,9-dimethoxy-1,4-methanonaphth-5,8-ylene acetate.

40 g. of 1,2,3,4-tetrachloro-1,4-dihydro-5,8-dihydroxy-1,4-methanonaphthalene-9-one dimethyl acetal, prepared according to Example 56 were mixed with 50 ml. of acetic anhydride and cooled by an ice bath and then a few drops of concentrated $H_2SO_4$ were added. The reaction was exothermic and the solution became clear. After ten minutes the solution solidified. The crude solid was washed on a Buchner funnel with Skelly "B"/acetone (50/50) and recrystallized from benzene/Skelly "B" (50/50) to give white crystals, m.p. 145°–146° C.

The product has the following structure:

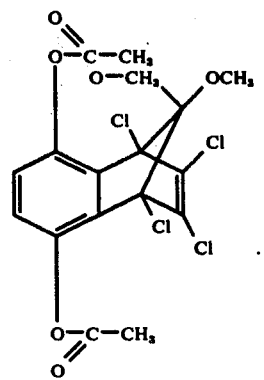

EXAMPLE 59

Reaction product of 1,2,3,4,12,12-hexachloro-1,4,4a,5,8,8a,9a,10a-octahydre-1,4:5,8-dimethanoanthracene-9,10-dione and $NaBH_4$.

45 g. of 1,2,3,4,12,12-hexachloro-1,4,4a,5,8,8a,9a,10a-octahydro-1,4:5,8-dimethanoanthracene-9,10-dione, prepared as in Example 46, were dissolved in 300 ml. of ethanol and 3 g. (slight excess) of NaBH₄ were added in small increments. The reaction temperature was maintained below 40° C by external cooling. After two hours stirring, the reaction mixture was concentrated to one-third its volume and poured into a water-ether mixture. The ether layer was separated and dried. Evaporation of the ether yielded a white solid. Even though the solid was recrystallized twice from benzene/Skelly B (50/50) it still gave a broad melting point range, 205°–210° C. Infrared spectrum showed strong —OH at 0600 cm⁻¹ and nmr agreed reasonably well with a 1,2,3,4,12,12-hexachloro-1,4,4a,5,8,8a,9-,9a,10,10a-decahydro-1,4:5 8-dimethanoantracene-9,10-diol (cis/trans)structure.

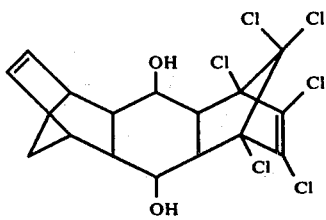

EXAMPLE 60

Preparation of 1,2,3,4,9,9-hexachloro-1,4,4a,5,6,7,8,8a-octahydro-1,4-methanonaphthalene-6-carbonitrile.

3-Cyclohexene-1-carbonitrile (Aldrich Chemical Corp.) (56 g.), and 200 g. of hexachlorocyclopentadiene were mixed, heated at 160°–170° C. for 6 hours, and then allowed to cool to room temperature. The reaction mixture was then vacuum distilled. Unreacted hexachlorocyclopentadiene was first removed and then the crude adduct produced was collected, 175°–170° C. at 0.3 m.m. Hg. The thick liquid was crystallized very slowly in Skelly "B". The crude solid melted at 140°–150° C.

The product has the following structure:

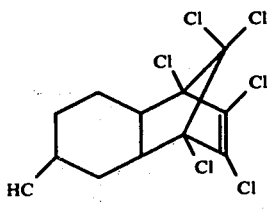

EXAMPLE 61

Preparation of 1,2,3,4,7,7-hexachloro-5-(2-acetoxy-benzyl)-2-norbornene 17.6 g of freshly distilled 2-allyl acetoxy benzene and 30 g. of hexachlorocyclopentadiene were mixed and heated at 170°–190° C for 5 hours and then the excess hexachlorocyclopentadiene was distilled off. The residue was a waxy material (pale yellow). This waxy material was used for fire retardant tests without further purification.

The product has the following structure:

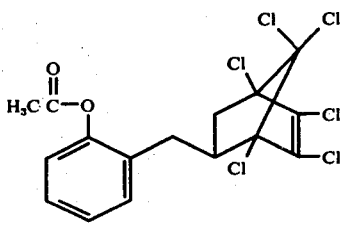

The following examples illustrate the fire retardant effect of various compounds on a number of polymers. Unless otherwise indicated the blends were prepared by mixing the compound and polymer in a conventional two roll mixing mill at the temperature and for the time specified. The compounded material was then molded to ⅛ inch thickness in a press at the temperature and for the time specified. The molded sheets, after cooling, were cut into strips and the strips were tested for fire retardance using the test specified.

EXAMPLES 62–137

A series of samples comprising compositions of ABS gum plastic containing a number of the foregoing described fire retardant compounds were prepared by milling the fire retardant compound and the ABS plastic at 320° F for 5 minutes. Test strips were prepared and were then evaluated for fire retardance using either ASTM method D-635, hereinafter referred to as "burn rate" and/or ASTM method D-2863, hereinafter referred to as "oxygen index". For the burn rate, the test strips were ⅛ inch × ½ inch × 5 inches and for the oxygen index, the test strips were ⅛ inch × ¼ inch × 2 ½ inches.

The ABS gum plastic used was a gum plastic containing 22% acrylonitrile, 23% butadiene and 55% styrene.

The results of the fire retardance tests are set forth in Table 1. (In the tables, SE means self-extinguishing.)

Table 1

| Example | Compound Prepared in Example No. | Amounts (parts) | ABS Plastic (parts) | Halogen Content % wt. | Burn Rate (in/min.) | Oxygen Index % |
|---|---|---|---|---|---|---|
| 62 | — | 0 | 100 | 0 | 1.8 | 18.3 |
| 63 | 1 | 8.7 | " | 4.5 | SE | — |
| 64 | 1 | 11.6 | " | 5.8 | SE | — |
| 65 | 1 | 15.0 | " | 7.5 | SE | — |
| 66 | 2 | 8.7 | " | 4.5 | 1.11 | — |
| 67 | 2 | 11.6 | " | 5.8 | SE | — |
| 68 | 2 | 15.4 | " | 7.5 | SE | — |
| 69 | 2 | 25.0 | " | 11.2 | SE | — |
| 70 | 3 | 7.1 | " | 3.7 | 1.03 | — |
| 71 | 3 | 8.7 | " | 4.5 | SE | — |
| 72 | 3 | 15.4 | " | 7.5 | SE | — |
| 73 | 4 | 15.4 | " | 7.0 | 0.61 | — |
| 74 | 5 | 15.4 | " | 8.7 | 1.40 | — |

Table 1-continued

| Example | Compound Prepared in Example No. | Amounts (parts) | ABS Plastic (parts) | Halogen Content % wt. | Burn Rate (in/min.) | Oxygen Index % |
|---|---|---|---|---|---|---|
| 75 | 6 | 8.5 | " | 5.2 | 1.28 | — |
| 76 | 8 | 10.0 | " | 4.4 | — | 23.7 |
| 77 | 9 | 15.4 | " | 6.6 | 0.73 | — |
| 78 | 10 | 16 | " | 6.2 | 1.47 | — |
| 79 | 10 | 20 | " | 7.5 | SE | — |
| 80 | 11 | 25 | " | 6.2 | SE | — |
| 81 | 14 | 11.4 | " | 4.3 | 0.72 | — |
| 82 | 15 | 16 | " | 7.0 | 0.66 | — |
| 83 | 16 | 8.7 | " | 3.7 | 1.28 | — |
| 84 | 16 | 15.4 | " | 6.1 | SE | — |
| 85 | 16 | 18.5 | " | 7.2 | SE | — |
| 86 | 17 | 18.5 | 100 | 6.7 | 1.33 | |
| 87 | 17 | 25 | " | 8.6 | SE | |
| 88 | 18 | 20 | " | 5.2 | 1.52 | |
| 89 | 18 | 40 | " | 8.9 | SE | |
| 90 | 19 | 20 | " | 6.5 | 1.45 | |
| 91 | 19 | 30 | " | 8.9 | SE | |
| 92 | 20 | 14 | " | 7.8 | 1.71 | |
| 93 | 20 | 16 | " | 8.7 | SE | |
| 94 | 21 | 16 | " | 5.6 | SE | |
| 95 | 22 | 18.4 | " | 7.0 | SE | |
| 96 | 25 | 14 | " | 7.3 | SE | |
| 97 | 26 | 18 | " | 7.6 | SE | |
| 98 | 27 | 25 | " | 8.3 | SE | |
| 99 | 28 | 24 | " | 7.1 | 1.28 | |
| 100 | 29 | 21.5 | " | 7.1 | SE | |
| 101 | 30 | 16 | " | 6.2 | 1.3 | |
| 102 | 31 | 14.7 | " | 9.5 | 0.98 | |
| 103 | 35 | 25 | " | 7.9 | SE | |
| 104 | 36 | 10 | " | 4.4 | | 23.66 |
| 105 | 37 | 15 | " | 5.0 | | 21.64 |
| 106 | 40 | 18.4 | " | 8.1 | 0.8 | |
| 107 | 41 | 18.4 | " | 6.0 | SE | |
| 108 | 42 | 18.4 | " | 6.87 | SE | |
| 109 | 43 | 18.4 | " | 8.4 | SE | |
| 110 | 44 | 16 | " | 6.7 | 1.13 | |
| 111 | 45 | 15.4 | 100 | 7.3 | SE | — |
| 112 | 46 | 15.4 | " | 6.4 | — | 24.50 |
| 113 | 46 | 15.4 +4.6Sb$_2$O$_3$ | " | 6.1 | SE | 27.30 |
| 114 | 47 | 20 | " | 8.4 | 0.69 | — |
| 115 | 48 | 26 | " | 14.7 | SE | — |
| 116 | 49 | 20.1 | " | 7.9 | 1.21 | 21.20 |
| 117 | 49 | 15.0 +4.6Sb$_2$O$_3$ | " | 6.0 | SE | 25.68 |
| 118 | 50 | 16.0 | " | 6.8 | 1.50 | 21.82 |
| 119 | 50 | 15.0+ 3.8Sb$_2$O$_3$ | " | 6.2 | 1.00 | 25.47 |
| 120 | 51 | 19.3 | " | 9.5 | 1.66 | 20.58 |
| 121 | 51 | 13.8 + 3.0Sb$_2$O$_3$ | " | 6.4 | 0.99 | 26.91 |
| 122 | 53 | 25 | " | 7.3 | 1.63 | — |
| 123 | 54 | 15.3 | " | 6.3 | 1.5 | — |
| 124 | 54 | 24 | " | 9.1 | 1.45 | — |
| 125 | 56 | 25 | " | 7.7 | 1.97 | — |
| 126 | 57 | 15.4 | " | 6.7 | 1.93 | — |
| 127 | 58 | 30 | " | 7.7 | 1.91 | — |
| 128 | 59 | 19.3 | " | 8.2 | 1.45 | 23.45 |
| 129 | 59 | 12.1+ 4.5Sb$_2$O$_3$ | " | 4.9 | SE | 28.25 |
| 130 | 60 | 20 | " | 9.0 | 1.38 | — |
| 131 | 63 | 25 | " | 9.3 | 1.40 | — |
| 132 | chloran | 15 | " | 6.7 | 1.50 | — |
| 133 | chloran | 25 | " | 10.0 | 1.24 | — |
| 134 | chlorendic anhydride | 15 | 100 | 7.7 | 1.30 | — |
| 135 | chlorendic anhydride | 20 | " | 9.6 | 1.19 | 20.8 |
| 136 | chlorendic anhydride | 25 | " | 11.5 | .78 | — |
| 137 | chlorendic anhydride | 30 | " | 13.3 | — | 21.4 |

The fire retardant effect of the structural system of the present invention, i.e., the 1,2,3,4,9,9-hexahalo-1,4-dihydro-1,4-methanonaphthalene-5,8-dione or 1,2,3,4,9,9-hexahalo-1,4-dihydro-1,4-methanonaphthalene-5,8-dioxy nucleus or a compound which is capable of being converted to the 1,2,3,4,9,9-hexahalo-1,4-dihydro-1,4-methanonaphthalene-5,8-dione nucleus, is clearly evident from the results in Table 1. The compounds of Examples 1–51 and 59 all possess the structural requirements of the fire retardant system of the present invention. These compounds differ, however, with respect to the ease of conversion of the 5,8-dioxy ring to the 1,2,3,4,9,9-hexahalo-1,4-dihydro-1,4-methanonaphthalene-5,8-dione system. Thus, for example, the compounds of Examples 1, 2 and 3, having the structures

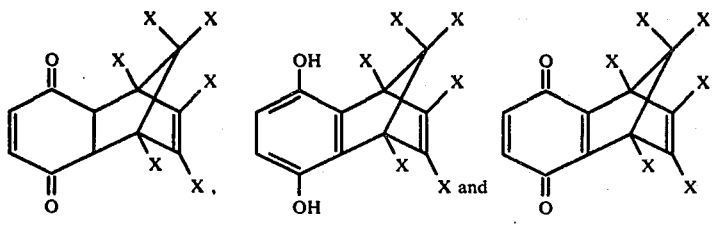

respectively, are effective fire retardants at relatively low concentration levels.

The compounds of Examples 5-8,10-12,24,25,31,36,45,47 and 48, which contain the required nucleus and also have additional substituents such as alkyl, halogen, sulfonyl, etc. attached to this nucleus, are slightly less effective than the unsubstituted compounds. Nevertheless, these compounds do possess significant flame retardant properties. The slight decrease in effectiveness is most probably due to the "diluting" effect of the additional substituents. Also, the compounds of Examples 4 and 9, wherein the dione structure is in the form of an oxime, possess excellent flame retardant properties.

In the compounds of Examples 13–23, 26–30, 32–35 and 37–39, the dioxy component is in the form of an ether or ester group. Such system is somewhat more difficult to convert to the 1,2,3,4,9,9-hexahalo-1,4-dihydro-1,4-methanonaphthalene-5,8-dione system. Thus, these compounds, while possessing substantial fire retardant properties, are not so effective as the compounds of Examples 6, 10–12,25,31,36 and 48.

Note that as the molecular weight of the ether or ester group increases, such as, for example, in the compounds of Examples 28 and 30, the effectiveness of the compound as a fire retardant decreases, again due most probably to "dilution".

All of the foregoing described compounds possess at least some unsaturation in the methano naphthalene ring system. If, however, the 5,8-dioxy structure is present in the unbridged six membered ring in the form of either carbonyl or hydroxyl groups but the ring is completely saturated a further slight decrease in fire retardant properties is observed. Such a result is, of course, entirely consistent with the foregoing, inasmuch as such compounds are more difficult, in terms of the "activation energy" required, to convert to the 1,2,3,4,9,9-hexahalo-1,4-dihydro-1,4-methanonaphthalene-5,8-dione structure. Even so the compounds of this class, illustrated by the compounds of Examples 40–44,46,49,50,51 and 59, do possess substantial fire retardant properties.

The compounds of Examples 53–58, 60, 61 and the known commercial fire retardants, chloran and chlorendic anhydride illustrate the critical effect on the fire retardant properties of a given compound of divergence from the structural components of the present system. Thus, compounds of Examples 53,55,56,57 and 58 do possess the 5,8-dioxy naphthalene nucleus, but do not contain a dihalomethano bridge. The compound of Examples 60 and chloran possess the 1,2,3,4,9,9-hexahalo-1,4-dimethano naphthalene nucleus but do not contain 5,8-dioxy substituent. In the compounds of Example 54 and chlorendic anhydride heteroatom ring systems replace the carbocyclic naphthalene ring system. In Example 61, the hexachloro norbornene ring and the oxybenzene ring units are separated by a methylene group rather than being fused into the naphthalene ring system. Consequently, each of these compounds possesses substantially less fire retardant capability than do the compounds containing the system of the present invention.

EXAMPLES 137–143

A series of samples were prepared by blending the fire retardant of Example 2 with a natural rubber formulation. The natural rubber formulation was as follows:

|  | Parts by weight |
|---|---|
| Smoked sheet | 100 |
| Zinc Oxide | 5 |
| Stearic Acid | 2 |
| Diphenylguanidine | 0.25 |
| N-cyclohexyl-2-benzothiazole-sulfonamide | 0.75 |
| Sulfur | 2 |

The blending was effected as follows:

A two-thirds portion of the rubber, zinc oxide and stearic acid were mixed on a warm mill (150°–160° F) for 5–8 minutes; the diphenylguanidine, N-cyclohexyl-2-benzothiazolesulfenamide, and sulfur were then blended with the remaining one-third portion of rubber for 5–8 minutes on a cool mill. The two mixtures were then combined with the fire retardant of Example 2 on a cool mill until well blended. The compounded stock was then cured 45 minutes at 292° F.

The samples thus prepared were subjected to burn rate tests. The results of these tests are set out in Table 2.

Table 2

| Example | Compound Prepared in Example No. | Amounts (parts) | Natural Rubber (parts) | Halogen Content, % wt. | Burn Rate (in/min) |
|---|---|---|---|---|---|
| 137 | 2 | None | 110 | 0 | 2.35 |
| 138 | 2 | 10 | 110 | 4.7 | 2.05 |
| 139 | 2 | 15 | 110 | 6.7 | 1.73 |
| 140 | 2 | 20 | 110 | 8.6 | 1.16 |
| 141 | 2 | 25 | 110 | 10.3 | SE |
| 142 | 2 | 30 | 110 | 12.0 | SE |
| 143 | 2 | 35 | 110 | 13.5 | SE |

The results in Table 2 show the excellent fire retardant effect of the present system on the highly combustible natural rubber.

EXAMPLES 144–147

A series of samples were prepared by blending the fire retardant of Example 2 with a butyl rubber formulation. The butyl rubber formulation was as follows:

|  | Parts |
|---|---|
| *Butyl 218 | 100 |
| Zinc Oxide | 5 |
| Stearic Acid | 2 |
| Mercaptobenzothiazole | 1.0 |
| Tet-amethyl thiuram disulfide | 1.5 |
| Sulfur | 1.25 |

*Butyl 218 (Enjay) is a medium unsaturated copolymer of isobutyl-lene-isoprene having a specific gravity of 0.92 and a Mooney viscosity, ML-3 0 260° F. of 50–60.

The blending was effected as follows:
Two-thirds of the rubber was mixed with the zinc oxide and stearic acid on a warm mill (150° F–160° F) for 5–8 minutes. The remaining one-third of the rubber was mixed with the mercaptobenzothiazole, tetramethyl thiuram disulfide, and sulfur on a cool mill for 5–8 minutes. The two mixtures were then combined with the fire retardant of Example 2 on a cool mill until well blended. The compounded stock was then cured 40 minutes at 320° F. The samples thus prepared were burn rate and oxygen index tested. The results of these tests are set out in Table 3.

| Example | Compound Prepared in Example No. | Amounts (parts) | Butyl Rubber (parts) | Halogen Content, % wt. | Burn Rate (in/min.) | Oxygen Index % |
|---|---|---|---|---|---|---|
| 144 | — | — | 110.75 | — | 2.14 | 18.23 |
| 145 | 2 | 10 | " | 4.6 | 1.63 | 19.01 |
| 146 | 2 | 20 | " | 8.6 | 1.17 | 20.06 |
| 147 | 2 | 30 | " | 11.9 | 1.49 | 22.10 |

EXAMPLES 148–158

A series of samples were prepared by blending the fire retardant of Example 2 of chlorendic anhydride with nylon polymers. Both "Nylon 6" nylon (Gulf) and "Zytel 63" nylon, a (du Pont) terpolymer of 6, 6:6 and 6:10 were utilized.

The samples prepared from Nylon 6 were milled at 420–430° F for 4–5 minutes, and molded at 430° 5 minutes.

The samples prepared from the nylon terpolymer were milled at 285° F for 3 minutes and molded at 285° F for 5 minutes.

The samples thus prepared were subjected to burn rate tests. The results of these tests are set out in Table 4.

Table 4

| Example | Compound Prepared in Example No. | Amounts (parts) | Polymer (parts) | Halogen Content % wt. | Burn Rate (in/min) |
|---|---|---|---|---|---|
| 148 | — | — | Zytel 63 100 | — | 0.54 |
| 149 | — | — | " | — | 0.55 |
| 150 | 2 | 2.5 | " | 1.4 | 0.59 |
| 151 | 2 | 5.0 | " | 2.7 | SE |
| 152 | 2 | 7.5 | " | 3.9 | Non-Burning |
| 153 | 2 | 15.4 | " | 7.5 | Non-Burning |
| 154 | Chlorendic Anhydride | 7.5 | " | 4.0 | SE |
| 155 | Chlorendic Anhydride | 15.4 | " | 7.7 | SE |
| 156 | — | — | Nylon 6 100 | — | 0.57 |
| 157 | 2 | 5.0 | " | 2.7 | 0.48 |
| 158 | 2 | 10.0 | " | 5.1 | SE |

From the data in Table 4 it is clear that the system of the present invention is a superior fire retardant for nylon as compared with the prior art fire retardant chlorendic anhydride. Thus, whereas, in Zytel terpolymer, the chlorendic anhydride is self-extinguishing (Examples 154 and 155), the system of the present invention, when used at the same levels, renders the polymer essentially non-burning (Examples 152 and 153).

EXAMPLES 159–165

A series of samples were prepared by blending the fire retardants of Examples 2 or 3 with polymethylacrylate. The polymethylacrylate was prepared by room temperature autopolymerization of methylacrylate.

The samples were milled at 200° F for 5 minutes and molded at 212° F. for 5 minutes.

The samples thus prepared were subjected to burn rate tests. The results of these tests are set out in Table 5.

Table 5

| Example | Compound Prepared in Example No. | Amounts (parts) | Polymethylacrylate | Halogen Content, % wt. | Burn Rate (in/min.) |
|---|---|---|---|---|---|
| 159 | — | — | 100 | — | 1.08 |
| 160 | 2 | 10 | 100 | 5.1 | 0.02 |
| 161 | 2 | 15 | 100 | 7.3 | 0.55 |
| 162 | 2 | 20 | 100 | 9.3 | 0.56 |
| 163 | 2 | 25 | 100 | 11.2 | 0.65 |
| 164 | 3 | 15 | 100 | 7.3 | SE |
| 165 | 3 | 25 | 100 | 11.3 | 0.76 |

The results in Table 5 show the marked effect of the fire retardant system of the present invention on polymethylacrylate. Thus, the compound of Example 2 markedly reduces the burn rate of polymethylacrylate (compare Example 159 with Examples 160–163), and the compound of Example 3 renders the polymethylacrylate essentially self-extinguishing (Example 164).

EXAMPLES 166–172

A series of samples were prepared by blending the fire retardant of Example 2 with a styrene-butadiene rubber formulation. The styrene-butadiene rubber formulation was as follows:

|  | Parts |
|---|---|
| *SB-R-1500 | 100 |

-continued

| | Parts |
|---|---|
| Zinc Oxide | 5 |
| Stearic Acid | 2 |
| Diphenylguanidine | 0.25 |
| N-cyclohexyl-2-benzothiazole sulfenamide | 1.0 |
| Sulfur | 2.0 |

*SB-R-1500 is a cold type, emulsion polymerized styrene-butadiene copolymer having a 22.5-24.50 wt. bound styrene, a specific gravity of 0.940 and a raw viscosity, ML-4 at 212° F of 46-58.

A two-thirds portion of the rubber, zinc oxide and stearic acid were mixed on a warm mill (150°–160° F) for 5–8 minutes. Next, diphenylquanidine, N-cyclohexyl-2-benzothiozole-sulfenamide, and sulfur were blended with the remaining one-third portion of rubber for 5–8 minutes on a cool mill. The two mixtures were then combined with the fire retardant of Example 2 on a cool mill until well blended. The compounded stock was then cured 45 minutes at 292° F.

The samples thus prepared were subjected to burn rate tests. The results of these tests are set out in Table 6.

Table 6

| Compound Example | Prepared in Example No. | Amounts (parts) | Styrene-butadiene rubber (parts) | Halogen Content % wt. | Burn Rate (in/min.) |
|---|---|---|---|---|---|
| 166 | — | — | 110.25 | — | 1.97 |
| 167 | 2 | 5 | " | 2.4 | 1.76 |
| 168 | 2 | 10 | " | 4.7 | 1.35 |
| 169 | 2 | 15 | " | 6.7 | 1.39 |
| 170 | 2 | 20 | " | 8.6 | 1.43 |
| 171 | 2 | 25 | " | 10.3 | 1.53 |
| 172 | 2 | 35 | " | 13.5 | 1.46 |

The results in Table 6 show that the fire retardant system of the present invention can reduce the burn rate of highly combustible styrene-butadiene rubber by about 25%. (Compare Example 166 with Examples 168 and 169.)

EXAMPLES 173–188

A series of samples were prepared by blending chlorendic anhydride, one of the fire retardants of Examples, 1, 2, 31 or 45, and a 70/30 styrene-acrylonitrile resin.

The samples were blended on a rubber mill at 310° F for 7 minutes and molded at 310° F for 5 minutes.

The samples thus prepared were subjected to burn rate tests. The results of these tests are set out in Table 7.

Table 7

| Compound Example | Prepared in Example No. | Amounts (parts) | Styrene-acrylonitrile resin (parts) | Halogen Content % wt. | Burn Rate (in/min.) |
|---|---|---|---|---|---|
| 173 | — | — | 100 | — | 1.12 (avg. of two) |
| 174 | 1 | 10 | " | 5.1 | 0.98 |
| 175 | 1 | 20 | " | 9.3 | 0.71 |
| 176 | 1 | 30 | " | 12.9 | 0.82 |
| 177 | 2 | 15.4 | " | 7.5 | 0.76 |
| 178 | 2 | 15.4 | " | 7.5 | 0.62 |
| 179 | 2 | 25 | " | 11.2 | 0.62 |
| 180 | 2 | 25 | " | 11.2 | 0.76 |
| 181 | 31 | 10 | " | 6.7 | 0.53 |
| 182 | 31 | 20 | " | 12.4 | SE |
| 183 | 31 | 30 | " | 17.1 | SE |
| 184 | 45 | 10 | " | 4.9 | 0.89 |
| 185 | 45 | 20 | " | 9.0 | 0.80 |
| 186 | 45 | 30 | " | 12.5 | 0.63 |
| 187 | Chlorendic anhydride | 15.4 | " | 7.7 | 0.77 |
| 188 | Chlorendic anhydride | 25 | " | 11.5 | 0.69 |

The results of Table 7 show that the fire retardant system of the present invention is at least as effective a fire retardant in styrene-acrylonitrile resin as is the prior art's chlorendic anhydride. Note the compound of Example 31 is markedly superior to chlorendic anhydride. (Compare Examples 181 and 182 with Examples 187 and 188.)

EXAMPLES 189–214

A series of samples were prepared by blending chlorendic anhydride or one of the fire retardants of Examples 1, 2 and 3 with polypropylene of varying molecular weights. The polypropylene had the following characteristics:

| Type | Molecular Weight | Melt flow rate* (dg/min) |
|---|---|---|
| A | 220,000 | 15.0 |
| B | 325,000 | 4.0 |
| C | 380,000 | 2.0 |
| D | 470,000 | 0.8 |
| E | 550,000 | 0.4 |

*Determind by ASTM D-1238-65T.

The samples were milled at 345° F for 4 minutes and molded at 350° F for 5 minutes.

The samples thus prepared were subjected to burn rate tests. The results of these tests are set out in Table 8.

TABLE 8

| Ex. | Compound Prepared in Example No. | Amounts (parts) | Polypropylene Type | Polypropylene Parts | Halogen Content, % wt. | Burn Rate (in/min.) |
|---|---|---|---|---|---|---|
| 189 | — | — | C | 100 | — | 0.70 |
| 190 | 1 | 11.6 | " | " | 5.8 | 0.67 |
| 191 | 1 | 15.4 | " | " | 7.5 | 0.46 |
| 192 | 1 | 15.4 | " | " | 7.5 | SE |
| 193 | 1 | 25.0 | " | " | 11.1 | SE |
| 194 | Chlorendic anhydride | 15.4 | " | " | 7.7 | 0.40 |
| 195 | — | — | " | " | — | 1.03 |
| 196 | 2 | 10 | " | " | 5.1 | 0.87 |
| 197 | 2 | 15 | " | " | 7.3 | 0.66 |
| 198 | 2 | 20 | " | " | 9.3 | 0.79 |
| 199 | 2 | 25 | " | " | 11.2 | SE |
| 200 | 3 | 10 | " | " | 5.1 | 0.70 |
| 201 | 3 | 15 | " | " | 7.3 | 0.66 |
| 202 | 3 | 20 | " | " | 0.93 | 0.67 |
| 203 | — | — | A | 100 | — | 1.26 |
| 204 | 2 | 15 | " | " | 7.3 | 0.61 |
| 205 | 2 | 20 | " | " | 9.3 | 0.84 |
| 206 | — | — | B | 100 | — | 1.12 |
| 207 | 2 | 15 | " | " | 7.3 | 0.58 |
| 208 | 2 | 20 | " | " | 9.3 | 0.59 |
| 209 | — | — | D | 100 | — | 1.38 |
| 210 | 2 | 15 | " | " | 7.3 | 0.59 |
| 211 | 2 | 20 | " | " | 9.3 | 0.58 |
| 212 | — | — | E | 100 | — | 1.28 |
| 213 | 2 | 15 | " | " | 7.3 | 0.71 |

TABLE 8-continued

| Ex. | Compound Prepared in Example No. | Amounts (parts) | Polypropylene Type | Parts | Halogen Content, % wt. | Burn Rate (in/min.) |
|---|---|---|---|---|---|---|
| 214 | 2 | 20 | " | " | 9.3 | 0.54 |

As shown in Table 8, the fire retardant system of the present invention substantially reduces the flammability of polypropylene.

EXAMPLES 215–230

A series of samples were prepared by blending the fire retardant of Example 2 or chlorendic anhydride with Marlex 6050, a (Phillips) high molecular weight, high density, linear homopolymer of ethylene.

The samples prepared from polyethylene were milled at 325° F for 5 minutes, and molded at 340° F for 5 minutes.

The samples thus prepared were subjected to the oxygen index test. The results of these tests are set out in Table 9.

TABLE 9

| Example | Compound Prepared in Example No. | Amounts (parts) | Polymer (parts) | | Halogen Content % wt. | Oxygen Index % |
|---|---|---|---|---|---|---|
| 215 | — | — | Marlex 6050 | 100 | — | 17.7 |
| 216 | 1 | 10 | " | " | 5.1 | 22.2 |
| 217 | " | 20 | " | " | 9.3 | 20.7 |
| 218 | " | 30 | " | " | 12.9 | 21.7 |
| 219 | 2 | 5 | " | " | 2.7 | 20.5 |
| 220 | " | 10 | " | " | 5.1 | 22.1 |
| 221 | " | 15 | " | " | 7.3 | 24.0 |
| 222 | " | 20 | " | " | 9.3 | 23.1 |
| 223 | " | 25 | " | " | 11.2 | 23.1 |
| 224 | 3 | 15 | " | " | 7.3 | 21.4 |
| 225 | " | 25 | " | " | 11.3 | 20.5 |
| 226 | Chlorendic anhydride | 5 | " | " | 2.7 | 19.1 |
| 227 | " | 10 | " | " | 5.2 | 19.6 |
| 228 | " | 15 | " | " | 7.5 | 19.4 |
| 229 | " | 20 | " | " | 9.6 | 20.9 |
| 230 | " | 25 | " | " | 11.5 | 21.1 |

EXAMPLES 231–241

A series of samples were prepared by blending the fire retardant of Example 2 or 3 with ethylene-vinylacetate copolymer, EVA (DQD-1868). The ethylene-vinylacetate copolymer had the following characteristics:

| Type | Shore A Hardness | Specific Gravity | Softening Point |
|---|---|---|---|
| EVA (DQD-1868) (18% vinyl acetate) | 88 | .943 | 64° C |

The samples were milled at 170° F for 5 minutes and molded at 212° F for 5 minutes.

The samples thus prepared were subjected to the oxygen index test. The results of these tests are set out in Table 10.

TABLE 10

| Example | Compound Prepared in Example No. | Amounts (parts) | Polymer (parts) | | Halogen Content % wt. | Oxygen Index % |
|---|---|---|---|---|---|---|
| 231 | — | — | EVA (DQD-1868) | 100 | — | 18.8 |
| 232 | 2 | 5 | " | " | 2.7 | 19.4 |
| 233 | " | 10 | " | " | 5.1 | 22.7 |
| 234 | " | 15 | " | " | 7.3 | 28.4 avg. of 2 |
| 235 | " | 20 | " | " | 9.3 | 27.2 |
| 236 | " | 25 | " | " | 11.2 | 29.8 |
| 237 | " | 35 | " | " | 14.5 | 27.4 avg. of 2 |
| 238 | 3 | 15 | " | " | 7.3 | 20.5 |
| 239 | " | 25 | " | " | 11.3 | 20.6 |
| 240 | Chlorendic anhydride | 15.4 | " | " | 7.7 | 20.8 |
| 241 | " | 25 | " | " | 11.5 | 21.2 |

EXAMPLES 242–245

A series of samples were prepared by blending the fire retardant of Example 2 with Elvanol 50–42, a (DuPont) high molecular weight, cold water soluble polyvinyl alcohol resin, having a 4% aqueous solution viscosity of 35–45 at 20° C as determined by the Hoeppler falling ball method.

The polyvinyl alcohol was ground to 60 mesh and dry mixed with the fire retardant of Example 2 ground to 200 mesh. The dry mixture was compression molded at 400° F for 5 minutes.

The samples thus prepared were subjected to oxygen index tests. The results of these tests are set out in Table 11.

TABLE 11

| Ex. | Compound Prepared in Example No. | Amounts (parts) | Polyvinyl alcohol (parts) | Halogen Content % wt. | Oxygen Index % |
|---|---|---|---|---|---|
| 242 | — | — | 100 | — | 22.48 |
| 243 | 2 | 5 | " | 2.7 | 23.29 |
| 244 | 2 | 10 | " | 5.1 | 25.46 |
| 245 | 2 | 15 | " | 7.3 | 28.73 |

EXAMPLES 246–286

A series of samples were prepared by blending either chlorendic anhydride or chloran or one of the fire retardants of Examples 1, 2, 3, 25, 31 and 45, with four different types of polystyrene. These polystyrenes were:

| Type | | Melt Viscosity (poises) | Izod impact res. (ft.lb/in notch at 73° F) | Hardness Rockwell M | Specific Gravity | Softening Point |
|---|---|---|---|---|---|---|
| A | high heat, general purpose | 2,700 | 0.20 | 71 | 1.04 | 220° F |
| B | high heat, general purpose | 3,200 | 0.25 | 76 | 1.04 | 224° F |
| C | impact polystyrene | 2,850 | 0.90 | 38 | 1.05 | 190° F |
| D | high heat, general purpose | 1,800 | 0.20 | 71 | 1.04 | 212° F |

Samples were also prepared by blending polystyrene, the fire retardant of Example 2 and antimony oxide ($Sb_2O_3$) in varying amounts.

The samples were milled at 330° F for 5 minutes and molded at 320° F for 5 minutes.

The samples thus prepared were subjected to burn rate and oxygen index tests. The results of these tests are set out in Table 12.

TABLE 12

| Example | Compound Prepared in Example No. | Amounts (parts) | Polystyrene type | (parts) | Halogen Content % wt. | Burn Rate (in/min.) | Oxygen Index % |
|---|---|---|---|---|---|---|---|
| 246 | — | — | A | 100 | 0 | 0.88 | 17.6 |
| 247 | 2 | 15.4 | " | " | 7.5 | SE | — |
| 248 | 2 | 25.0 | " | " | 11.2 | SE | — |
| 249 | Chlorendic anhydride | 15.4 | " | " | 7.7 | 0.91 | 20.4 |
| 250 | Chlorendic anhydride | 25.0 | " | " | 11.5 | 0.60 | 18.9 |
| 251 | — | — | C | " | 0 | — | 17.8 |
| 252 | 2 | 17.7 | " | " | 8.4 | — | 25.9 |
| 253* | 2 | 11.6 | " | " | 5.6 | — | 25.9 |
| 254* | 2 | 19.0 | " | " | 8.4 | — | 26.7 |
| 255 | Chloran | 20.5 | " | " | 8.5 | — | 19.6 |
| 256* | Chloran | 21.5 | " | " | 8.9 | — | 25.8 |
| 257 | — | — | B | " | 0 | 1.34 | — |
| 258 | 1 | 10 | " | " | 5.1 | 1.11 | — |
| 259 | 1 | 13 | " | " | 7.3 | 0.90 | — |
| 260 | 1 | 20 | " | " | 9.3 | 0.64 | — |
| 261 | 2 | 5 | " | " | 2.7 | 1.12 | — |
| 262 | 2 | 10 | " | " | 5.1 | 1.07 | — |
| 263 | 2 | 20 | " | " | 9.3 | 0.58 | — |
| 264 | 2 | 25 | " | " | 11.2 | Non-burning | — |
| 265 | 3 | 5 | " | " | 2.7 | 1.22 | — |
| 266 | 3 | 10 | " | " | 5.1 | 1.18 | — |
| 267 | 3 | 15 | B | " | 7.3 | SE | — |
| 268 | 25 | 15 | B | 100 | 7.8 | SE | — |
| 269 | 31 | 10 | " | " | 6.7 | Non-burning | — |
| 270 | 31 | 15 | " | " | 9.5 | Non-burning | — |
| 271 | 45 | 10 | " | " | 4.9 | 0.97 | — |
| 272 | 45 | 15 | " | " | 7.0 | 0.71 | — |
| 273 | 45 | 20 | " | " | 9.0 | 0.82 | — |
| 274 | Chlorendic anhydride | 15 | " | " | 7.5 | 1.26 | — |
| 275 | Chlorendic anhydride | 25 | " | " | 11.5 | 0.70 | — |
| 276 | — | — | D | " | 0 | 1.11 | — |
| 277 | 2 | 5 | " | " | 2.7 | 0.87 | — |
| 278 | 2 | 10 | " | " | 5.1 | 0.73 | — |
| 279 | 2 | 15 | " | " | 7.3 | 0.84 | — |
| 280 | 2 | 15 | " | " | 7.3 | 0.71 | — |
| 281 | 2 | 20 | " | " | 9.3 | 0.68 | — |

TABLE 12-continued

| Example | Compound Prepared in Example No. | Amounts (parts) | Polystyrene type | (parts) | Halogen Content % wt. | Burn Rate (in/min.) | Oxygen Index % |
|---|---|---|---|---|---|---|---|
| 282 | 2 | 25 | " | " | 11.3 | 0.57 | — |
| 283 | 3 | 15 | " | " | 7.3 | 0.65 | — |
| 284 | 3 | 25 | " | " | 11.3 | SE | — |
| 285 | Chlorendic anhydride | 15 | " | " | 7.5 | 1.20 | — |
| 286 | Chlorendic anhydride | 25 | " | " | 11.5 | 1.13 | — |

*In Examples 253, 254 and 256, the compounds also contained 4.7, 7.6 and 5.1 parts, respectively, of $Sb_2O_3$.

From Table 12, it is apparent that the addition of relatively small amounts of antimony oxide substantially enhances the effect of the fire retardant system of the present invention. Thus, identical oxygen index values are obtained in Example 252 and Example 253, even though the polymer of Example 253, which contained $Sb_2O_3$, contained 1/3 less of the fire retardant of Example 2 than did the polymer of Example 252.

EXAMPLES 287–291

A series of samples were prepared by blending either the fire retardant of Example 2 or chlorendic anhydride with poly-alpha-methyl-styrene. The poly-alpha-methyl-styrene had a number average molecular weight of 100,000.

The samples were milled at 330° F for 7 minutes and molded at 330° F for 5 minutes.

The samples thus prepared were subjected to burn rate tests. The results of these tests are set out in Table 13.

TABLE 13

| Ex. | Compound Prepared in Example No. | Amounts (parts) | Poly-alpha-methyl-styrene (parts) | Halogen Content, % wt. | Burn Rate (in/min.) |
|---|---|---|---|---|---|
| 287 | — | — | 100 | 0 | 2.49 |
| 288 | 2 | 15 | 100 | 7.3 | 2.09 |
| 289 | 2 | 25 | 100 | 11.2 | 1.89 |
| 290 | Chlorendic anhydride | 15 | 100 | 7.5 | 2.11 |
| 291 | Chlorendic anhydride | 25 | 100 | 11.5 | 1.88 |

The results in Table 13 show that in poly-alpha-methyl-styrene, the system of the present invention is at least as effective as chlorendic anhydride.

EXAMPLES 292–294

A series of samples were prepared by blending the fire retardant of Example 2 with a polysulfone. The polysulfone was prepared from bisphenol-A and dichlorodiphenyl sulfone and had a heat distortion temperature of 181° C at 66 psi.

The samples were milled at 450° F for 10 minutes and molded at 450° F for 5 minutes.

The samples thus prepared were subject to burn rate and oxygen index tests as hereinabove described. The results of these tests are set out in Table 14.

TABLE 4

| Ex. | Compound Prepared in Example No. | Amounts (parts) | Polysulfone (parts) | Halogen Content % wt. | Burn Rate (in/min.) | Oxygen Index % |
|---|---|---|---|---|---|---|
| 292 | — | — | 100 | 0 | Non Burning | 32.4 |
| 293 | 2 | 7.5 | 100 | 3.9 | " | 45.2 |
| 294 | 2 | 15.4 | 100 | 7.5 | " | 32.0 |

The results in Table 14 show that although the unprotected polysulfone is non-burning by the burn rate test, there is a marked decrease in flammability as measured by the oxygen index test of a polysulfone containing the fire retardant system of the present invention. Note, however, that the fire retardancy does not continue to increase with increasing halogen content. Thus, the flammability of the polysulfone containing the fire retardant system is lowest at a level of 7.5 parts of the system per 100 parts of polysulfone. As the amount of fire retardant system in the polysulfone is increased, however, the flammability of the composition increases.

EXAMPLES 295–297

A series of samples were prepared by blending the fire retardant of Example 2 with a polycarbonate. The polycarbonate was a thermoplastic carbonate linked polymer obtained from the reaction of bisphenol-A and phosgene and having a heat distortion temperature of 143° C at 66 psi.

The samples were milled at 500°–550° F for 10 minutes and molded at 500°–550° F for 5 minutes.

The samples thus prepared were subjected to burn rate and oxygen index tests as described hereinabove. The results of these tests are set out in Table 15.

TABLE 15

| Ex. | Compound Prepared in Example No. | Amounts (parts) | Polycarbonate (parts) | Halogen Content, % wt. | Burn Rate (in/min.) | Oxygen Index % |
|---|---|---|---|---|---|---|
| 295 | — | — | 100 | 0 | SE | 24.8 |
| 296 | 2 | 7.5 | 100 | 3.9 | SE | 29.9 |
| 297 | 2 | 15.4 | 100 | 7.5 | SE | 26.7 |

As shown in Table 15 the flammability of the polycarbonate polymer is reduced when the fire retardant system of the present invention is blended therewith.

EXAMPLES 298–302

A series of samples were prepared by blending the fire retardant of Example 2 or chlorendic anhydride with a cellulose ester. The cellulose ester was prepared from cellulose acetate butyrate. (Tenite Butyrate-Eastman).

The samples were milled at 350° F for 4 minutes and molded at 350° F for 5 minutes.

The samples thus prepared were subjected to burn rate tests. The results of these tests are set out in Table 16.

TABLE 16

| Ex. | Compound Prepared in Example No. | Amounts (parts) | Cellulose Ester (parts) | Halogen Content, % wt. | Burn Rate (in/min.) |
|---|---|---|---|---|---|
| 298 | — | — | 100 | 0 | 0.89 |
| 299 | 2 | 15.4 | 100 | 7.5 | 0.73 |
| 300 | 2 | 25 | 100 | 11.2 | 0.69 |
| 301 | Chlorendic Anhydride | 15.4 | 100 | 7.7 | 0.90 |
| 302 | Chlorendic Anhydride | 25 | 100 | 11.5 | 0.86 |

The results in Table 16 show the superiority of the fire retardant system of the present invention in a cellulose ester polymer as compared with the effect of chlorendic anhydride in such polymer.

EXAMPLES 303–305

A series of samples were prepared by blending the fire retardants of Examples 1 and 2 with polyvinylchloride plasticized with dioctylphthalate.

The samples were milled at 315° F for 5 minutes and molded at 315° F for 5 minutes.

The samples thus prepared were subjected to burn rate tests. The results of these tests are set out in Table 17.

TABLE 17

| Example | Compound Prepared in Example No. | Amounts (parts) | Plasticized polyvinylchloride PVC (parts) | dioctyl phthalate (parts) | Halogen Content % wt. | Burn Rate (in/min.) |
|---|---|---|---|---|---|---|
| 303 | — | — | 100 | 100 | 28.4 | burned |
| 304 | 1 | 8 | " | " | 29.4 | SE |
| 305 | 2 | 5 | " | " | 29.0 | 1.25 |

The results in Table 17 show the marked decrease in the flammability of plasticized polyvinylchloride when the fire retardant system of the present system is blended therewith. This effect is particularly significant in view of the increased use of plasticized polyvinylchloride polymers for high temperature uses such as crash pads and the like.

EXAMPLES 306–316

A series of samples were prepared by blending the fire retardant of Examples 2 and 45 with two types of epoxy resin. One epoxy resin was the condensation product of epichlorohydrin and bisphenol A (Epon 815, Shell), and the other was the epoxide of bis-cyclopentenyl ether (ERLA 4305).

The samples were prepared by mixing the epoxy resin with the fire retardant compound and meta-phenylene diamine at 176° F, curing the Epon 815 resin for 2 hours at 212° F and then for 2 hours at 300° F, and curing the ERLA 4305 resin for 2 hours at 212° F and then for 16 hours at 310° F.

The samples thus prepared were subjected to burn rate tests. The results of these tests are set out in Table 18.

TABLE 18

| Example | Compound Prepared in Example No. | Amounts (parts) | Epoxy Resin Type | Parts | Meta-phenylene diamine | Halogen Content % wt. | Burn Rate (in/min.) |
|---|---|---|---|---|---|---|---|
| 306 | — | — | Epon 815 | 87.5 | 12.5 | 0 | 0.76 avg. of 2 |
| 307 | 2 | 5 | " | " | " | 2.7 | SE |
| 308 | 2 | 10 | " | " | " | 5.1 | SE |
| 309 | 2 | 20 | " | " | " | 9.3 | 0.97 |
| 310 | 45 | 5 | " | " | 12.7 | 2.7 | SE |
| 311 | 45 | 10 | " | " | " | 5.1 | SE |
| 312 | | | ERLA 4305 | 86 | 14 | 0 | 0.78 avg. of 2 |
| 313 | 2 | 5 | " | " | " | 2.7 | 0.86 |
| 314 | 2 | 10 | " | " | " | 5.1 | 0.83 |
| 315 | 2 | 15 | " | " | " | 7.3 | SE |
| 316 | 2 | 20 | " | " | " | 9.3 | Non-Burning |

The results in Table 18 show the fire retardant effect of the system of the present invention on two different types of epoxy resin. Note that in the Epon 815, the maximum effect is obtained at a level of 5–10 parts of fire retardant compound to 87.5 parts of resin.

EXAMPLES 317–318

A series of samples were prepared by blending the fire retardant of Example 2 with polyethylene terephthalate having an intrinsic viscosity of 0.93 in 60/40 phenol-tetrachlorethane.

The samples were milled at 500° F for 10 minutes and molded at 500° F for 5 minutes.

The samples thus prepared were subjected to burn rate tests. The results of these tests are set out in Table 19.

TABLE 19

| Ex. | Compound Prepared in Example No. | Amounts (parts) | Polyethylene terephthalate (parts) | Halogen Content % wt. | Burn Rate (in/min.) |
|---|---|---|---|---|---|
| 317 | — | — | 100 | 0 | 0.56 |
| 318 | 2 | 15.4 | 100 | 7.5 | SE |

The results in Table 19 demonstrate the marked decrease in flammability of polyethyleneterephthalate when blended with the fire retardant system of the present invention.

EXAMPLES 319–355

A series of samples were prepared by blending chlorendic anhydride or one of the fire retardants of Examples 1,2,3,25,31,45, and 47 with a liquid cast polyurethane based on castor oil (Type C) or on Thanol F-3000, i.e., a polypropylene ether glycol (Type D) or with a thermoplastic polyurethanes based on polyether (Type A; Roylar A-855; Uniroyal) and based on polyester (Type B; Roylar S-4; Uniroyal). Roylar A-855 is a high hardness urethane thermoplastic which is based on polytetramethylene ether glycol and has a hardness of 91A and a specific gravity of 1.12. Roylar S-4 has a hardness of 40D and a specific gravity of 1.23.

Type C liquid cast polyurethanes were prepared by dissolving the fire retardant and 0.1 part of triethylene diamine (catalyst) in the CO (castor oil-Baker Castor Oil Co., D.B. grade). The solution was cooled to 40° C and TD1 (80/20 ratio of 2,4- and 2,6- toluene diisocyanate isomers) was mixed in by rapid stirring. The mixture was immediately poured into a 6×6×⅛ inch mold and cured for one hour at 140° C.

Type D liquid cast polyurethanes were prepared similarly except that the castor oil was replaced by Thanol F-3000 (Jefferson Chem. Co. polypropylene glycol of 3000 molecular weight and 1000 hydroxyl equivalent weight) and the Thanol solution was cooled at 80° C before mixing in TD1.

The samples with Type A were milled at 335° F for 4 minutes and molded at 350° F for 5 minutes. The samples with Type B were milled at 380° F for 4 minutes and molded at 350° F for 5 minutes.

The samples thus prepared were subjected to burn rate tests. The results of these tests are set out in Table 20.

TABLE 20

| Example | Compound Prepared in Example No. | Amounts (parts) | Polyurethane Type | Polyurethane (parts) | Halogen Content, % wt. | Burn Rate (in/min.) |
|---|---|---|---|---|---|---|
| 319 | — | — | A | 100 | 0 | 1.12 Average of two |
| 320 | 2 | 5 | " | " | 2.7 | SE |
| 321 | 2 | 10 | " | " | 5.1 | Non Burning |
| 322 | 2 | 15.4 | " | " | 7.5 | Non Burning |
| 323 | 2 | 25 | " | " | 11.2 | Non Burning |
| 324 | 3 | 10 | " | " | 5.1 | " |
| 325 | 3 | 15 | " | " | 7.3 | " |
| 326 | 31 | 15 | " | " | 9.5 | 1.38 |
| 327 | 31 | 25 | " | " | 14.8 | 1.52 |
| 328 | 45 | 5 | " | " | 2.6 | 0.87 |
| 329 | 45 | 10 | " | " | 4.9 | Non Burning |
| 330 | 45 | 15 | " | " | 7.0 | Non Burning |
| 331 | 47 | 15 | " | " | 6.4 | 1.36 |
| 332 | 47 | 25 | " | " | 9.9 | 1.44 |
| 333 | Chlorendic anhydride | 15.4 | " | " | 7.7 | 0.68 |
| 334 | Chlorendic anhydride | 25.0 | " | " | 11.5 | 0.80 |
| 335 | — | — | C | CO 82.0 TDI 21.8 | | 1.80 |
| 336 | 1 | 10 | C | CO 82.0 TDI 21.8 | 4.9 | 1.21 |
| 337 | 1 | 15 | C | CO 82.0 TDI 21.8 | 7.1 | 1.07 |
| 338 | 1 | 20 | C | CO 82.0 TDI 21.8 | 9.0 | 0.87 |
| 339 | 2 | 5 | " | CO 77.2 TDI 23.0 | 2.7 | 0.69 |
| 340 | 2 | 10 | " | CO 75.3 TDI 24.9 | 5.1 | 0.74 |
| 341 | 2 | 15 | " | CO 73.4 TDI 26.8 | 7.3 | SE |
| 342 | 2 | 20 | " | CO 71.5 TDI 28.7 | 9.3 | SE |
| 343 | 2 | 25 | " | CO 69.5 TDI 30.6 | 11.3 | SE |
| 344 | 47 | 10 | " | CO 82.0 TDI 21.8 | 4.3 | 1.20 |
| 345 | 47 | 15 | " | CO 82.0 TDI 21.8 | 6.4 | 1.01 |
| 346 | | | D | Thanol 92.0 TDI 8.0 | 0 | 1.71 |
| 347 | 2 | 10 | " | Thanol 88.0 | 5.1 | 0.70 |

TABLE 20-continued

| Example | Compound Prepared in Example No. | Amounts (parts) | Polyurethane Type | Polyurethane (parts) | Halogen Content, % wt. | Burn Rate (in/min.) |
|---|---|---|---|---|---|---|
| 348 | 2 | 15 | '' | TDI 12.2 Thanol 85.5 TDI 14.4 | 7.3 | SE |
| 349 | — | — | B | 100 | 0 | 0.94 avg. of 2 |
| 350 | 2 | 15.2 | '' | '' | 7.5 | SE |
| 351 | 2 | 25 | '' | '' | 11.2 | SE |
| 352 | 3 | 10 | '' | '' | 5.1 | SE |
| 353 | 3 | 15 | '' | '' | 7.3 | SE |
| 354 | 25 | 10 | '' | '' | 5.4 | SE |
| 355 | 25 | 15 | '' | '' | 7.8 | SE |

As shown in Table 20, the effect of the fire retardant system of the present invention on a polyurethane based polyether, i.e., Type A., is substantial, inasmuch as at relatively low levels of fire retardant compound the polymer is rendered completely non-burning. For polyurethanes based on castor oil, (Type C), Thanol F3000, (Type D), and polyurethanes based on polyesters, (Type B), when blended with the fire retardant system of the present invention, the polyurethane is rendered either self-extinguishing or the flammability thereof is substantially decreased.

EXAMPLES 356–358

A series of samples were prepared by blending the fire retardant of Example 2 with BKR-2620, (Union Carbide) a predominantly unmodified, heat reactive phenol-formaldehyde resin having a specific gravity of 25° C of 1.23–1.25, a softening point of 180°–210° F by the ball and ring method, and a Gardner Color (1933 scale) of 12 maximum on a 50% solids solution in ethanol.

The phenol-formaldehyde resin was ground to 200 mesh and dry mixed with the fire retardant of Example 2 to 200 mesh. The dry mixture was compression molded at 350° F for 30 minutes.

The samples thus prepared were subjected to oxygen index tests. The results of these tests are set out in Table 21.

TABLE 21

| Ex. | Compound Prepared in Example No. | Amount (parts) | Phenol-formaldehyde resin (parts) | Halogen Content % wt. | Oxygen Index % |
|---|---|---|---|---|---|
| 356 | — | — | 100 | — | 24.57 |
| 357 | 2 | 5 | '' | 2.7 | 26.67 |
| 358 | 2 | 10 | '' | 5.1 | 27.88 |

Variations and modifications can, of course, be made without departing from the spirit and scope of the present invention.

What is claimed is:

1. A compound having the formula:

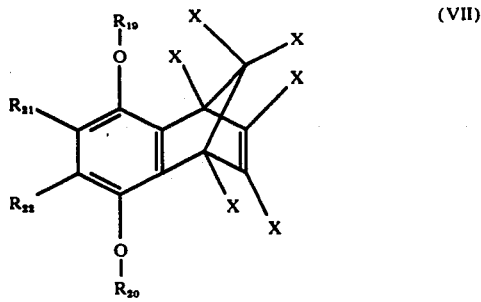

(VII)

wherein $R_{19}$ and $R_{20}$ are both

wherein $R_{29}$ is lower alkyl, $R_{21}$ and $R_{22}$ are both hydrogen and X is halogen.

2. A compound as claimed in claim 1, wherein $R_{29}$ is methyl and X is chlorine.

3. A compound as claimed in claim 1, wherein $R_{29}$ is ethyl and X is chlorine.

4. A compound as claimed in claim 1, wherein $R_{29}$ is nonyl and X is chlorine.

5. A compound as claimed in claim 1, wherein $R_{29}$ is tert-butyl and X is chlorine.

6. A compound as claimed in claim 1, wherein $R_{29}$ is methyl and X is bromine.

* * * * *

UNITED STATES PATENT OFFICE
CERTIFICATE OF CORRECTION

Patent No. 4,009,200    Dated 2/22/77

Inventor(s) Julian R. Little et al

It is certified that error appears in the above-identified patent and that said Letters Patent are hereby corrected as shown below:

Title page, the title: "-1,4-METHANO-NAPTH-" should read -- 1,4-METHANO-NAPHTH- --; under "Related U.S. Application Data": "Ser. No. 80,747, Oct. 14, 1974" should read -- Ser. No. 80,747, Oct. 14, 1970 --; line 4 of the Abstract: "-1,4-dihydro-1,4:methanonapthalene-" should read -- 1,4-dihydro-1,4-methanonaphthalene- --; line 8 of the Abstract: "exert is function." should read -- exert its function. --.

Column 1, lines 1-2, the title: "-1,4-METHANO-NAPTH-" should read -- -1,4-METHANO-NAPHTH- --.

Column 6, line 48: "$R_{17}$ and $R_{13}$" should read -- $R_{17}$ and $R_{18}$ --; line 49: "$R_{17}$ and $R_{13}$" should read -- $R_{17}$ and $R_{18}$ --.

Column 7, line 65: "than" should read -- then --.

Column 8, lines 19-26:

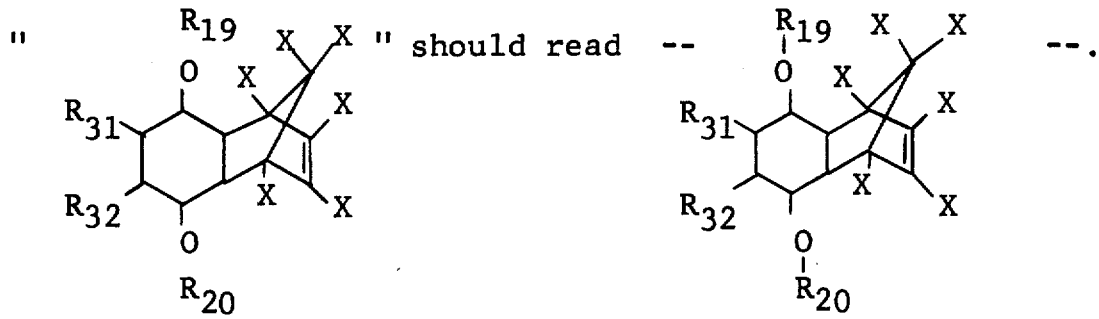

UNITED STATES PATENT OFFICE
CERTIFICATE OF CORRECTION

Patent No. 4,009,200                Dated 2/22/77

Inventor(s) Julian R. Little et al

It is certified that error appears in the above-identified patent and that said Letters Patent are hereby corrected as shown below:

Column 11, line 17: "examples of (e.g., adipic starting" should read -- examples of suitable starting --.

Column 12, line 25: "2,2bis(4-hydroxyphenyl)propane," should read -- 2,2-bis(4-hydroxyphenyl)propane, --.

Column 16, lines 51-52: "2,3diamino-2-methylbutane," should read -- 2,3-diamino-2-methylbutane, --.

Column 22, lines 20-21: "-9a-hexahydro-dimethanoanthracene-9,10-dione" should read -- -9a-hexahydro-1,4:5,8-dimethano-anthracene-9,10-dione --; line 35: "0.33" should read -- 0.53 --

Column 23, lines 64-65: "1,2,3,4,9,9-hexachloro-1,4,a,8a-" should read -- 1,2,3,4,9,9-hexachloro-1,4,4a,8a- --.

Column 32, lines 53-54: "-heptachloro-1,4,4a8a-tetrahydro-" should read -- -heptachloro-1,4,4a,8a-tetrahydro- --.

Column 33, lines 16-17: "methanonaphthalene-5,8-diol. Skellysolve recrystallized 12.5°" should read -- methanonaphthalene-5,8-diol. --.

Column 36, lines 59-60: "1,3cyclopentadiene" should read -- 1,3-cyclopentadiene --.

Column 40, line 62: "salicyclic" should read -- salicylic --.

UNITED STATES PATENT OFFICE
CERTIFICATE OF CORRECTION

Patent No. 4,009,200           Dated 2/22/77

Inventor(s) Julian R. Little et al

It is certified that error appears in the above-identified patent and that said Letters Patent are hereby corrected as shown below:

Column 41, line 9: "C 48.3%" should read -- C 48.34% --.

Column 45, lines 45-46: "1,4-methanoaphthalene-5,8-diol." should read -- 1,4-methanonaphthalene-5,8-diol. --.

Column 47, lines 15-16: "1,2,3,4,5,7,12,12-" should read -- 1,2,3,4,6,7,12,12- --; lines 17-18: "-1,4,4a,5,8,8a,9a,1-0a-" should read -- -1,4,4a,5,8,8a,9a,10a- --.

Column 50, lines 63-64: "-1,4,4a,5,8,8a,9a,10a-octahydre-" should read-- -1,4,4a,5,8,8a,9a,10a-octrahydro- --; lines 66-68 "-1,4,4a,5,8,8a,9a,1-0a-" should read-- -1,4,4a,5,8,8a,9a,10a- --.

Column 51, line 11: "0600 $cm^{-1}$" should read -- 3600 $cm^{-1}$ --.

Columns 53-54, Table 1, column 5, line 6: "6.2" should read -- 8.2 --; Table 1, Example 132:
"chloran 15        "        6.7        1.50        -" should read
--chloran        15        "        6.7        1.50        -  --.

Column 56, lines 31-32: "N-cyclohexyl-2-benzothiazole-sulfonamide" should read -- N-cyclohexyl-2-benzothiazole-sulfenamide --.

Column 57, line 7: "Tet-amethyl thiuram disulfide" should read -- Tetramethyl thiuram disulfide --; line 9: "isobutyl-lene-isoprene" should read -- isobutylene-isoprene --; line 10:

UNITED STATES PATENT OFFICE
CERTIFICATE OF CORRECTION

Patent No. 4,009,200     Dated 2/22/77

Inventor(s) Julian R. Little et al

It is certified that error appears in the above-identified patent and that said Letters Patent are hereby corrected as shown below:

"ML-3 0 260°F." should read:  -- ML-3  260°F. --; lines 43-44: "430° 5 minutes." should read -- 430°F. for 5 minutes. --.

Column 58, Table 5, column 6, line 2: "0.02" should read -- 0.82 --.

Column 59, line 10: "22.5-24.50" should read -- 22.5-24.5% --; line 15: "diphenylquanidine," should read -- diphenylguanidine, --.

Columns 59 and 60, Table 7, in the heading:

"
| Styrene- | | |
|---|---|---|
| Prepared in Example No. | Amounts (parts) | acrylonitrile resin (parts) |

" should read

| | Compound | |
|---|---|---|
| Prepared in Example No. | Amounts (parts) | Styrene acrylonitrile resin (parts) |

--.

Column 64, line 28: "320°F" should read -- 330°F --.

Columns 63-64, Table 12, column 3, line 14: "13" should read -- 15 --

UNITED STATES PATENT OFFICE
CERTIFICATE OF CORRECTION

Patent No. 4,009,200     Dated 2/22/77

Inventor(s) Julian R. Little et al

It is certified that error appears in the above-identified patent and that said Letters Patent are hereby corrected as shown below:

Columns 65-66, Table 12, column 6, line 1: "11.3" should read -- 11.2 --; Table 12, line 2 of footnote: "$Eb_2O_3$." should read -- $Sb_2O_3$. --; Table 13, last column, line 3: "1.89" should read -- 1.88 --.

Column 66, line 19: "TABLE 4" should read -- TABLE 14 --.

Signed and Sealed this

Eighteenth Day of October 1977

[SEAL]

Attest:

RUTH C. MASON
Attesting Officer

LUTRELLE F. PARKER
Acting Commissioner of Patents and Trademarks